United States Patent
Thierry et al.

(10) Patent No.: US 11,814,686 B2
(45) Date of Patent: Nov. 14, 2023

(54) METHOD FOR SCREENING AND TREATING A SUBJECT FOR A CANCER

(71) Applicants: INSERM (Institut National de la Santé et de la Recherche Médicale), Paris (FR); Université de Montpellier, Montpellier (FR); Institut Régional du Cancer de Montpellier, Montpellier (FR)

(72) Inventors: Alain Thierry, Montpellier (FR); Cynthia Sanchez, Montpellier (FR)

(73) Assignees: INSTITUT NATIONAL DE LA SANTÉDE LA RECHERCHE MÉDICALE, Paris (FR); UNIVERSITÉ de MONTPELLIER, Montpellier (FR); INSTITUT RéGIONAL DU CANCER DE MONTPELLIER, Montpellier (FR)

( * ) Notice: Subject to any disclaimer, the term of this patent is extended or adjusted under 35 U.S.C. 154(b) by 58 days.

(21) Appl. No.: 16/770,351

(22) PCT Filed: Dec. 6, 2018

(86) PCT No.: PCT/EP2018/083851
§ 371 (c)(1),
(2) Date: Jun. 5, 2020

(87) PCT Pub. No.: WO2019/110750
PCT Pub. Date: Jun. 13, 2019

(65) Prior Publication Data
US 2021/0172019 A1    Jun. 10, 2021

(30) Foreign Application Priority Data
Dec. 7, 2017   (EP) .................................... 17306721

(51) Int. Cl.
*C12Q 1/6886* (2018.01)
*C12Q 1/6806* (2018.01)

(52) U.S. Cl.
CPC ......... *C12Q 1/6886* (2013.01); *C12Q 1/6806* (2013.01); *C12Q 2600/112* (2013.01)

(58) Field of Classification Search
CPC .................................................. C12Q 1/6886

USPC ....................................................... 424/155.1
See application file for complete search history.

(56) References Cited

FOREIGN PATENT DOCUMENTS

| WO | 2001/042503 A2 | 6/2001 |
|---|---|---|
| WO | 2012/028746 A1 | 3/2012 |
| WO | 2015/181213 A1 | 12/2015 |
| WO | 2016/063122 A1 | 4/2016 |

OTHER PUBLICATIONS

Labianca et al. (Critical Reviews in Oncology/Hematology, 2004, 51: 145-170).*
Wang et al (Cancer Research, 2003, 63: 3966-3968).*
Jelovac et al (CA Cancer J Clin, 2011, 6: 183-203).*
Hortobagyi (NEJM, 1998, 33(14): 974-984).*
Umetani et al (J Clin Onc, 2006, 24: 4270-4276).*
Jiang et al.; "Lengthening and shortening of plasma DNA in hepatocellular carcinoma patients"; Proceedings of the National Academy of Sciences, vol. 112, No. 11, Feb. 2, 2015, pp. E1317-E1325.

* cited by examiner

*Primary Examiner* — Sean E Aeder
(74) *Attorney, Agent, or Firm* — WCF IP

(57) ABSTRACT

The present invention relates to the diagnostic of cancerous subject. Indeed, the inventors observed by using a Q-PCR based methods and sequencing methods that quantification of specific single stranded DNA fragments obtained from cell free nucleic acids (cfDNA) may discriminate cfDNA from healthy and cancer derived subjects. Single stranded DNA fragments obtained from CfDNA or specific range of single stranded DNA fragments are rather lower or higher when derived from healthy subject than from cancer subject. More, specific ratios for different size or range of single stranded DNA fragments varies between cancer subjects and healthy individuals. These values are sufficiently and significantly different to be used as values to determine whether a human subject may have cancer or not as a screening test. Thus, the invention relates to a method for screening a subject for a cancer comprising the steps of extracting and denaturing cfDNA, determining the single strand fragment level upon their size distribution, and calculate these former values to screen an individual for cancer.

3 Claims, 4 Drawing Sheets

METHOD FOR SCREENING AND TREATING A SUBJECT FOR A CANCER

FIELD OF THE INVENTION

Figure 1:
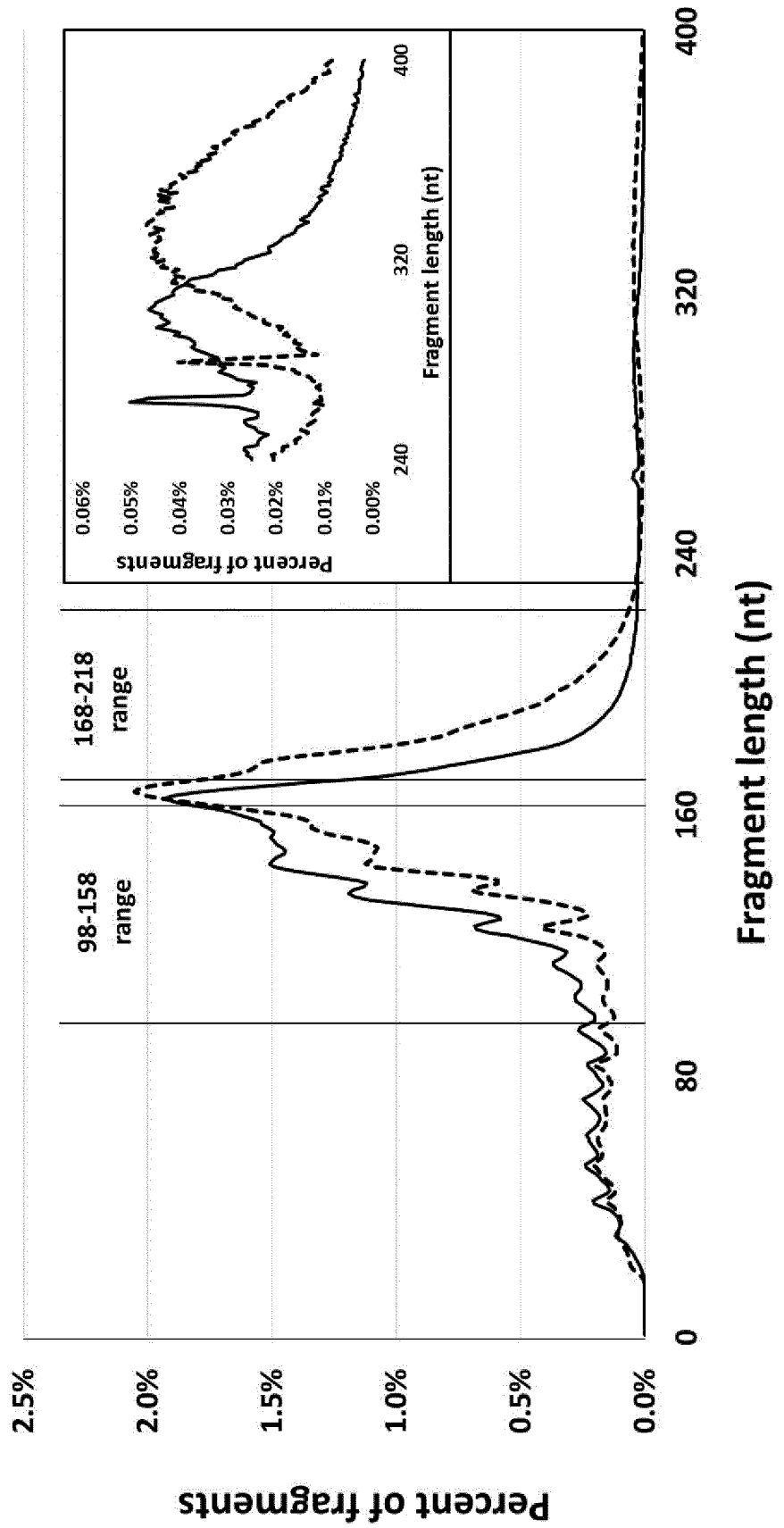

The present invention relates to a method for screening a subject for a cancer comprising the steps of based on the level of single stranded DNA fragments extracting and denaturing from cfDNA.

BACKGROUND OF THE INVENTION

The discovery of circulating cell-free DNA (cfDNA) in humans (1) has led to intensive research on its potential use in various clinical fields (1-5). CfDNA concentration is significantly increased in cancer subjects (6-8) and the observation that a proportion of cfDNA is tumor-derived has led to the concept of a 'liquid biopsy'; therefore, cfDNA analysis could provide diagnostic and prognostic information. Various groups are developing techniques that allow the detection and characterization of genetic and epigenetic alterations of tumor cells by analyzing cfDNA from the plasma or serum of cancer subjects (3,9). Such techniques could revolutionize the management of cancer by detecting mutations leading to resistance to targeted therapies, personalized therapeutic monitoring, and non-invasive follow-up of the disease. CfDNA analysis is currently used in prenatal diagnosis (10) and shows potential for clinical use in other fields including autoimmune diseases, organ transplant, trauma, sepsis, and myocardial infarction (1).

While cfDNA analysis appears clinically useful for several pathologies and specific physiological conditions, a precise understanding of its origins and nature, including the size distribution of cfDNA fragments, has not been established (1). Yet, it is imperative to have detailed information on the size distribution of cfDNA fragments, to determine the optimal cfDNA concentration and to obtain a high level of sensitivity and specificity, especially when detecting rare genetic alterations. Excluding mass spectrometry, all current methods of cfDNA analysis, including sequencing or PCR-based methods, require cfDNA size definition.

CfDNA structure and size depend on the mechanisms of cfDNA release from cells. While we do not know their respective proportions with regards to cfDNA amount shed into the blood stream, several have been proposed, including necrosis, apoptosis, phagocytosis, active release, and exosome/microparticles release (1.)

In addition to the diversity of cfDNA release mechanisms in the literature, discrepancies in cfDNA fragment size distribution in healthy individuals or cancer patients are apparent. The most reported size distribution is dominated by mono- and oligo-nucleosomes (11), and has become the basic premise concerning the structure of cfDNA for many years (1,12). In particular, conventional NGS methods, as well as earlier works based on electrophoretic mobility, such as PAGE or the Agilent platform, have revealed clearly a high proportion of cfDNA fragments ranging from 170 to 200 bp (13,14). Apoptotic DNA cleavage produces a characteristic pattern ladder of 180-200 bp, or multiples thereof (oligonucleosomes), and DNA fragmentation (25). DNA wrapped around the histone octamer is 147 bp in length and the linker DNA is 20-90 bp. Association of these fragments with nucleosomes presumably assures structural integrity by protecting DNA from enzymatic degradation in the circulatory system (16-18).

Contrarily, other studies have shown the presence of large-sized fragments of many kilobases (kbp), which may indicate a necrotic release mechanism. During necrosis, the chromatin chain is degraded in a disorganized manner leading to fragments of >50 kbp (15,19). Specifically, cfDNA fragments longer than 10 000 bp are likely to originate from necrotic cells, whereas DNA fragments shorter than 1000 bp, particularly 180 bp or multiples of this size, indicate the oligonucleosomal DNA ladder observed in apoptotic cells (15). However, these observations should be taken with caution because of the uncertainty of pre-analytical factors, especially with regard to the contamination of DNA derived from blood-cell degradation.

In contrast, the inventors have shown by alternative methods including a Q-PCR-based method and atomic force microscopy (AFM), the majority of cfDNA in cancer patients is less than 145 bp (8,20). They demonstrated, for the first time, by amplifying DNA sequences of increasing size within the same DNA region, the presence of a higher proportion of cfDNA fragments <100 bp directly correlating with an increase of cfDNA concentration (20). Moreover, this observation suggested that the detection of amplicons <100 bp is more relevant for optimally quantifying cfDNA (8). This has been confirmed and now most of the Q-PCR-based methods involve the amplification of DNA sequences <100 bp, while targeting ~150 bp length sequences is known to be optimal for quantifying non-fragmented genomic DNA (9,21,22).

SUMMARY OF THE INVENTION

Here, the inventors observed by using a Q-PCR based methods and sequencing methods that quantification of specific single stranded DNA fragments obtained from cell free nucleic acids (cfDNA) may discriminate cfDNA from healthy and cancer derived subjects. Single stranded DNA fragments obtained from CfDNA or specific range of single stranded DNA fragments are rather lower or higher when derived from healthy subject than from cancer subject. More, specific ratios for different size or range of single stranded DNA fragments varies between cancer subjects and healthy individuals. These values are sufficiently and significantly different to be used as values to determine whether a human subject may have cancer or not as a screening test.

Thus, the present invention relates to a method for screening a subject for a cancer comprising the steps of based on the level of single stranded DNA fragments extracting and denaturing from cfDNA. Particularly, the invention is defined by its claims.

DETAILED DESCRIPTION OF THE INVENTION

A first aspect of the invention relates to a method for screening a subject for a cancer comprising the steps of:
  i. extracting the cell free nucleic acids (cfDNA) from a sample obtained from the subject;
  ii. denaturating the cell free nucleic acids (cf DNA) to obtain single stranded DNA fragments;
  iii. determining the level of at least one single stranded DNA fragment having a length between 20 to 400 nucleotides;
  iv. comparing the level determined at step iii) with a predetermined reference value and;
  v. concluding that the subject suffers from a cancer when the level determined at step iii) differ from the predetermined reference value.

As used herein the term "sample" refers to any biological sample obtained from the subject that is liable to contain cell free nucleic acids. Typically, samples include but are not limited to body fluid samples, such as blood, ascite, urine, amniotic fluid, feces, saliva or cerebrospinal fluids. In some embodiments, the sample is a blood sample. By "blood sample" it is meant a volume of whole blood or fraction thereof, e.g., serum, plasma, etc. In one embodiment, the sample consists in culture supernatant of cells, embryo or organoid. Any methods well known in the art may be used by the skilled artisan in the art for extracting the free cell nucleic acid from the prepared sample. For example, the method described in the EXAMPLE may be used.

As used herein, the term "subject" denotes a mammal. Typically, a patient according to the invention refers to any subject (preferably human) afflicted with a cancer. The term "subject" also refers to a subject with no cancer.

As used herein, the term "single stranded DNA fragment" denote single stranded (compared to double stranded) fragment of DNA which can have different size of nucleic acids.

As used herein the terms the "level of at least one single stranded DNA fragment having a length between 20 to 400 nucleotides" denote the quantity (or concentration) of at least one single stranded DNA fragment of a specific size (e.g. of a specific length of nucleic) whatever the sequence of the fragments. For example the terms the "level of a single stranded DNA fragment having a length of 50 nucleotides" denotes the level (quantity or concentration) of all the single stranded DNA fragments having a length of 50 nucleotides whatever the sequence of the fragments of 50 nucleotides.

According to the invention, as used herein, the "level" means quantity, number or concentration of a fragment.

As used herein the term "nucleic acid" has its general meaning in the art and refers to refers to a coding or non-coding nucleic sequence. Nucleic acids include DNA (deoxyribonucleic acid) and RNA (ribonucleic acid) nucleic acids. Example of nucleic acid thus include but are not limited to DNA, mRNA, tRNA, rRNA, tmRNA, miRNA, piRNA, snoRNA, and snRNA. Nucleic acids thus encompass coding and non-coding region of a genome (i.e. nuclear or mitochondrial).

As used herein, the term "nuclear nucleic acid" has its general meaning in the art and refers to a nucleic acid originating from the nucleus of cell. The term nuclear nucleic acid encompasses all forms of the nucleic acids excepting those originating from the mitochondria. The term nuclear nucleic acid is thus defined in opposition to the term "mitochondrial nucleic acid". Mitochondria are indeed structures within cells that convert the energy from food into a form that cells can use. Although most DNA is packaged in chromosomes within the nucleus, mitochondria also have a small amount of their own DNA. This genetic material is known as "mitochondrial DNA" or "mtDNA". In humans, mitochondrial DNA spans about 16,500 DNA building blocks (base pairs), representing a small fraction of the total DNA in cells. Mitochondrial DNA contains 37 genes, all of which are essential for normal mitochondrial function: ATP6; ATP8; COX1; COX2; COX3; CYTB; ND1; ND2; ND3; ND4; ND4L; ND5; ND6; RNR1, RNR2 TRNA; TRNA; TRNC; TRND; TRNE; TRNF; TRNG; TRNI; TRNK; TRNL1; TRNL2; TRNM; TRNN; TRNN; TRNP; TRNQ; TRNR; TRNS1; TRNS2; TRNT; TRNV; TRNW; and TRNY. Genes encoding for NADH dehydrogenase (complex I) include MT-ND1, MT-ND2, MT-ND3, MT-ND4, MT-ND4L, MT-ND5, and MT-ND6. Genes encoding for Coenzyme Q-cytochrome c reductase/Cytochrome b (complex III) include MT-CYB. Gene encoding for cytochrome c oxidase (complex IV) include MT-CO1, MT-CO2, MT-CO3. Gene enconding for ATP synthase (complex V) include MT-ATP6, and MT-ATP8. Gene encoding for humanin include MT-RNR2 (encoding both ribosomal 16S and humanin). MT-RNR1 and MT-RNR2 genes providing instruction to produce ribosomal 12S and 16S respectively. The 22 species of mitochondrial tRNAs (mt tRNAs) encoded by mtDNA involved in mitochondrial protein synthesis machinery. Human mitochondrial DNA (mtDNA) has three promoters, H1, H2, and L (heavy strand 1, heavy strand 2, and light strand promoters). Mitochondrial genome also comprises control regions or d-loop sequences. Mitochondrial nuclear acids are known per se by the skilled person (e.g. NCBI Reference Sequence: NC_012920.1, SEQ ID NO:1). Thirteen of these genes provide instructions for making enzymes involved in oxidative phosphorylation. Oxidative phosphorylation is a process that uses oxygen and simple sugars to create adenosine triphosphate (ATP), the cell's main energy source. The remaining genes provide instructions for making molecules called transfer RNA (tRNA) and ribosomal RNA (rRNA), which are chemical cousins of DNA. These types of RNA help assemble protein building blocks (amino acids) into functioning proteins.

By "cell free nucleic acid" or "cfDNA" it is meant that the nucleic acid is released by the cell and present in the sample. In some embodiments, the cell free nucleic acid is circulating cell-free DNA (ccfDNA) and it is easy and routine for one of ordinary skill in the art to distinguish mitochondrial ccf nucleic acids" or "mitochondrial ccfDNA" from "nuclear ccfDNA". Actually, mitochondrial ccfDNA encompasses any DNA mitochondrial nucleic acid and in opposition nuclear ccfDNA encompasses any DNA nuclear nucleic acid.

In one embodiment, the method of the invention comprises the steps of:
  i. extracting the cell free nucleic acids from a sample obtained from the subject;
  ii. denaturating the cell free nucleic acids to obtain single stranded DNA fragments;
  iii. determining the level of a first single stranded DNA fragment having a length between 20 to 400 nucleotides;
  iv. determining the level of a second single stranded DNA fragment having a length between 20 to 400 nucleotides;
  v. calculating the ratio of the level determined at step iii) to the level determined at step iv) or alternatively the ratio of the level determined at step iv) to the level determined at step iii;
  vi. comparing the ratio determined at step v) with a predetermined corresponding reference value and;
  vii. concluding that the subject suffers from a cancer when the ratio determined at step v) differ from the predetermined corresponding reference value.

In another embodiment, the method of the invention comprises the steps of:
  i. extracting the cell free nucleic acids from a sample obtained from the subject;
  ii. denaturating the cell free nucleic acids to obtain single stranded DNA fragments;
  iii. determining the level of a first single stranded DNA fragment having a length inferior to 160 nucleotides (i.e. short size single stranded DNA fragment);
  iv. determining the level of a second single stranded DNA fragment having a length superior or equal to 160 nucleotides (i.e long size single stranded DNA fragment);

v. calculating the ratio of the level determined at step iii) to the level determined at step iv) or alternatively the ratio of the level determined at step iv) to the level determined at step iii;

vi. comparing the ratio determined at step v) with a predetermined corresponding reference value and;

vii. concluding that the subject suffers from a cancer when the ratio determined at step v) differ from the predetermined corresponding reference value.

As used herein, the term "single stranded DNA fragment having a length inferior to 160 nucleotides" denotes single stranded DNA fragment having a length inferior to 160 nucleotides and superior or equal to 20 nucleotides.

As used herein, the term "single stranded DNA fragment having a length superior to 160 nucleotides" denotes single stranded DNA fragment having a length superior or equal to 160 nucleotides and inferior or equal to 400 nucleotides.

As shown in the example (FIG. 1), the inventors demonstrated that between a length of 160 to 167 nucleotides, the levels of the nucleotides between a subject suffering from a cancer and a healthy subject are relatively the same. Thus, the peak (as used in the examples) that is to say the value of the length of fragments where the curve of the cancerous subjects and the curve of healthy subject are crossing (see FIG. 1) can correspond to fragments having a length of 160, 161, 162, 163, 164, 165, 166 or 167 nucleotides. These fragments (fragments having a length of 160, 161, 162, 163, 164, 165, 166 or 167 nucleotides) are also the most present (with the maximum level).

Thus, in another embodiment, the short size single stranded DNA fragment and the long size single stranded DNA fragment can be determined according the peak as defined above.

As used herein, the term "ratio of the level" denote the ratio between the levels of the single stranded DNA fragments determined in the steps of the method. According to the invention, the ratio may be the ratio between the level of the first single stranded DNA fragment and the level of the second single stranded DNA fragment (level of the first single stranded DNA fragment/level of the second single stranded DNA fragment) or the ratio between the level of the second single stranded DNA fragment and the level of the first single stranded DNA fragment (level of the second single stranded DNA fragment/level of the first single stranded DNA fragment).

Another aspect of the invention relates to a method for screening a subject for a cancer comprising the steps of:
i. extracting the cell free nucleic acids from a sample obtained from the subject;
ii. denaturating the cell free nucleic acids to obtain single stranded DNA fragments;
iii. determining the level of a group of single stranded DNA fragments on a specific range having a length between 20 to 400 nucleotides;
iv. comparing the level determined at step iii) with a predetermined reference value and;
v. concluding that the subject suffers from a cancer when the level determined at step iii) differ from the predetermined reference value.

As used herein, the terms "a group of single stranded DNA fragments on a specific rang" denote specific single stranded (compared to double stranded) fragments (more than one fragments) of DNA of different size of nucleic acids whatever the sequence of the fragments. As used herein, the terms "a group of single stranded DNA fragments on a specific range having a length between 20 to 400 nucleotides" denotes specific single stranded fragments (more than one fragments) of DNA of nucleic acids comprises between 20 and 400 nucleotides. It means that between the size of 20 to 400 nucleotides, more than one group of fragments can be selected and their level can be determined. For example, the level of the fragments of 22 nucleotides, the level of the fragments of 57 nucleotides and the level of the fragments of 156 nucleotides can be determined and compared to the a predetermined reference value. As used herein, the term "group" denotes that there is more than one single stranded DNA fragment and at least two single stranded DNA fragments.

According to this method, the level (e.g. the quantity) of the fragments of a group of (e.g. composed by) 2, 3, 4, 5, 6, 7, 8, 9, 10, 11, 12, 13, 14, 15, 16, 17, 18, 19, 20; 21; 22; 23; 24; 25; 26; 27; 28; 29; 30; 31; 32; 33; 34; 35; 36; 37; 38; 39; 40; 41; 42; 43; 44; 45; 46; 47; 48; 49; 50; 51; 52; 53; 54; 55; 56; 57; 58; 59; 60; 61; 62; 63; 64; 65; 66; 67; 68; 69; 70; 71; 72; 73; 74; 75; 76; 77; 78; 79; 80; 81; 82; 83; 84; 85; 86; 87; 88; 89; 90; 91; 92; 93; 94; 95; 96; 97; 98; 99; 100; 101; 102; 103; 104; 105; 106; 107; 108; 109; 110; 111; 112; 113; 114; 115; 116; 117; 118; 119; 120; 121; 122; 123; 124; 125; 126; 127; 128; 129; 130; 131; 132; 133; 134; 135; 136; 137; 138; 139; 140; 141; 142; 143; 144; 145, 146; 147; 148; 149; 150; 151; 152; 153; 154; 155; 156; 157; 158; 159; 160; 161; 162; 163; 164; 165; 166; 167; 168; 169; 170; 171; 172; 173; 174; 175; 176; 177; 178; 179; 180; 181; 182; 183; 184; 185; 186; 187; 188; 189; 190; 191; 192; 193; 194; 195; 196; 197; 198; 199; 200; 201; 202; 203; 204; 205; 206; 207; 208; 209; 210; 211; 212; 213; 214; 215; 216; 217; 218; 219; 220; 221; 222; 223; 224; 225; 226; 227; 228; 229; 230; 231; 232; 233; 234; 235; 236; 237; 238; 239; 240; 241; 242; 243; 244; 245; 246; 247; 248, 249; 250; 251; 252; 253; 256; 257; 258; 259; 260; 261; 262; 263; 264; 265; 266; 267; 268; 269; 270; 271; 272; 273; 274; 275; 276; 277; 278; 279; 281; 282; 283; 284; 285; 286; 287; 288; 289; 290; 291; 292; 293; 294; 295; 296; 297; 298; 299; 300; 301; 302; 303; 304; 305; 306; 307; 308; 309; 310; 311; 312; 313; 314; 315; 316; 317; 318; 319; 320; 321; 322; 323; 324; 325; 326; 327; 328; 329; 330; 331; 332; 333; 334; 335; 336; 337; 338; 339; 340; 341; 342; 343; 344; 345; 346; 347; 348; 349; 350; 351; 352; 353; 354; 355; 356; 357; 358; 359; 360; 361; 362; 363; 364; 365; 366; 367; 368; 369; 370; 371; 372; 373; 374; 375; 376; 377; 378; 379 or 380 fragments can be determined.

In one embodiment, the level of a group of single stranded DNA fragments can be determined in specific sub-group and particularly between 20 to 80 nucleotides, between 80 to 155 nucleotides and between 155 to 220 nucleotides whatever the sequences of the fragments. For example, the level of a group of single stranded DNA fragments can be determined in the sub-group of nucleotides having a length between 20 to 80 nucleotides. In this case, for example, the level of nucleotides having a length of 22 nucleotides, 45 nucleotides and 66 nucleotides can be determined.

In another embodiment, the invention relates to a method for screening a subject for a cancer comprising the steps of:
i. extracting the cell free nucleic acids from a sample obtained from the subject;
ii. denaturating the cell free nucleic acids to obtain single stranded DNA fragments;
iii. determining the level of a first group of single stranded DNA fragments on a specific range having a length between 20 to 400 nucleotides;
iv. determining the level of a second group of single stranded DNA fragments on a specific rang having a length between 20 to 400 nucleotides;

v. calculating the ratio of the level determined at step iii) to the level determined at step iv) or alternatively the ratio of the level determined at step iv) to the level determined at step iii;

vi. comparing the ratio determined at step v) with a predetermined corresponding reference value and;

vii. concluding that the subject suffers from a cancer when the ratio determined at step v) differ from the predetermined corresponding reference value.

In another embodiment, the invention relates to a method for screening a subject for a cancer comprising the steps of:

i. extracting the cell free nucleic acids from a sample obtained from the subject;

ii. denaturating the cell free nucleic acids to obtain single stranded DNA fragments;

iii. determining the level of a group of single stranded DNA fragments on a specific rang having a length inferior to 160 nucleotides (i.e. short size single stranded DNA fragment);

iv. determining the level of a group of single stranded DNA fragments on a specific rang having a length superior or equal to 160 nucleotides (i.e. long single stranded DNA fragment);

v. calculating the ratio of the level determined at step iii) to the level determined at step iv) or alternatively the ratio of the level determined at step iv) to the level determined at step iii;

vi. comparing the ratio determined at step v) with a predetermined corresponding reference value and;

vii. concluding that the subject suffers from a cancer when the ratio determined at step v) differ from the predetermined corresponding reference value.

As used herein, the term the "ratio of the level" denote the ratio between the levels of the group of single stranded DNA fragments determined in the steps of the method. According to the invention, the ratio may be the ratio between the level of the first group of single stranded DNA fragment and the level of the second group of single stranded DNA fragment (level of the first group of single stranded DNA fragment/level of second group of single stranded DNA fragment) or the ratio between the level of the second group of single stranded DNA fragment and the level of the first group of single stranded DNA fragment (level of the second group of single stranded DNA fragment/level of the first group of single stranded DNA fragment).

As used herein, the term "a group of single stranded DNA fragments on a specific rang having a length inferior to 160 nucleotides" denotes a group of single stranded DNA fragments having a length inferior to 160 nucleotides and superior or equal to 20 nucleotides.

As used herein, the term "a group of single stranded DNA fragments on a specific rang having a length superior or equal to 160 nucleotides" denotes a group of single stranded DNA fragment having a length superior to 160 nucleotides and inferior or equal to 400 nucleotides.

In another aspect of the invention, the ratio between the level of a group of single stranded DNA fragments on a specific range having a length between 20 to 400 nucleotides and the level of one single stranded DNA fragment having a length between 20 to 400 nucleotides can also be determined and compare to a predetermined reference value.

Thus in another aspect, the invention relates a method for screening a subject for a cancer comprising the steps of:

i. extracting the cell free nucleic acids from a sample obtained from the subject;

ii. denaturating the cell free nucleic acids to obtain single stranded DNA fragments;

iii. determining the level of a group of single stranded DNA fragments on a specific range having a length between 20 to 400 nucleotides;

iv. determining the level of one single stranded DNA fragment having a length between 20 to 400 nucleotides;

v. calculating the ratio of the level determined at step iii) to the level determined at step iv) or alternatively the ratio of the level determined at step iv) to the level determined at step iii;

vi. comparing the ratio determined at step v) with a predetermined corresponding reference value and;

vii. concluding that the subject suffers from a cancer when the ratio determined at step v) differ from the predetermined corresponding reference value.

In one embodiment, the single stranded DNA fragments may have having a length inferior to 160 nucleotides (i.e. short size single stranded DNA fragment) or may have a length superior or equal to 160 nucleotides (i.e. long size single stranded DNA fragment).

According to the methods of the invention, the single stranded DNA fragment can have a length of 20; 21; 22; 23; 24; 25; 26; 27; 28; 29; 30; 31; 32; 33; 34; 35; 36; 37; 38; 39; 40; 41; 42; 43; 44; 45; 46; 47; 48; 49; 50; 51; 52; 53; 54; 55; 56; 57; 58; 59; 60; 61; 62; 63; 64; 65; 66; 67; 68; 69; 70; 71; 72; 73; 74; 75; 76; 77; 78; 79; 80; 81; 82; 83; 84; 85; 86; 87; 88; 89; 90; 91; 92; 93; 94; 95; 96; 97; 98; 99; 100; 101; 102; 103; 104; 105; 106; 107; 108; 109; 110; 111; 112; 113; 114; 115; 116; 117; 118; 119; 120; 121; 122; 123; 124; 125; 126; 127; 128; 129; 130; 131; 132; 133; 134; 135; 136; 137; 138; 139; 140; 141; 142; 143; 144; 145; 146; 147; 148; 149; 150; 151; 152; 153; 154; 155; 156; 157; 158; 159; 160; 161; 162; 163; 164; 165; 166; 167; 168; 169; 170; 171; 172; 173; 174; 175; 176; 177; 178; 179; 180; 181; 182; 183; 184; 185; 186; 187; 188; 189; 190; 191; 192; 193; 194; 195; 196; 197; 198; 199; 200; 201; 202; 203; 204; 205; 206; 207; 208; 209; 210; 211; 212; 213; 214; 215; 216; 217; 218; 219; 220; 221; 222; 223; 224; 225; 226; 227; 228; 229; 230; 231; 232; 233; 234; 235; 236; 237; 238; 239; 240; 241; 242; 243; 244; 245; 246; 247; 248; 249; 250; 251; 252; 253; 256; 257; 258; 259; 260; 261; 262; 263; 264; 265; 266; 267; 268; 269; 270; 271; 272; 273; 274; 275; 276; 277; 278; 279; 280; 281; 282; 283; 284; 285; 286; 287; 288; 289; 290; 291; 292; 293; 294; 295; 296; 297; 298; 299; 300; 301; 302; 303; 304; 305; 306; 307; 308; 309; 310; 311; 312; 313; 314; 315; 316; 317; 318; 319; 320; 321; 322; 323; 324; 325; 326; 327; 328; 329; 330; 331; 332; 333; 334; 335; 336; 337; 338; 339; 340; 341; 342; 343; 344; 345; 346; 347; 348; 349; 350; 351; 352; 353; 354; 355; 356; 357; 358; 359; 360; 361; 362; 363; 364; 365; 366; 367; 368; 369; 370; 371; 372; 373; 374; 375; 376; 377; 378; 379; 380; 381; 382; 383; 384; 385; 386; 387; 388; 389; 390; 391; 392; 393; 394; 395; 396; 397; 398; 399 or 400 nucleotides.

According to the methods of the invention, the short size single stranded DNA fragment can have of a length of 20; 21; 22; 23; 24; 25; 26; 27; 28; 29; 30; 31; 32; 33; 34; 35; 36; 37; 38; 39; 40; 41; 42; 43; 44; 45; 46; 47; 48; 49; 50; 51; 52; 53; 54; 55; 56; 57; 58; 59; 60; 61; 62; 63; 64; 65; 66; 67; 68; 69; 70; 71; 72; 73; 74; 75; 76; 77; 78; 79; 80; 81; 82; 83; 84; 85; 86; 87; 88; 89; 90; 91; 92; 93; 94; 95; 96; 97; 98; 99; 100; 101; 102; 103; 104; 105; 106; 107; 108; 109; 110; 111; 112; 113; 114; 115; 116; 117; 118; 119; 120; 121; 122; 123; 124; 125; 126; 127; 128; 129; 130; 131; 132; 133; 134; 135; 136; 137; 138; 139; 140; 141; 142; 143; 144; 145; 146; 147; 148; 149; 150; 151; 152; 153; 154; 155; 156; 157; 158 or 159 nucleotides and the long size single stranded DNA fragment can have a length of 160; 161; 162; 163; 164; 165; 166; 167 168; 169; 170; 171; 172; 173; 174; 175; 176; 177; 178; 179;

180; 181; 182; 183; 184; 185; 186; 187; 188; 189; 190; 191; 192; 193; 194; 195; 196; 197; 198; 199; 200; 201; 202; 203; 204; 205; 206; 207; 208; 209; 210; 211; 212; 213; 214; 215; 216; 217; 218; 219; 220; 221; 222; 223; 224; 225; 226; 227; 228; 229; 230; 231; 232; 233; 234; 235; 236; 237; 238; 239; 240; 241; 242; 243; 244; 245; 246; 247; 248; 249; 250; 251; 252; 253; 256; 257; 258; 259; 260; 261; 262; 263; 264; 265; 266; 267; 268; 269; 270; 271; 272; 273; 274; 275; 276; 277; 278; 279; 280; 281; 282; 283; 284; 285; 286; 287; 288; 289; 290; 291; 292; 293; 294; 295; 296; 297; 298; 299; 300; 301; 302; 303; 304; 305; 306; 307; 308; 309; 310; 311; 312; 313; 314; 315; 316; 317; 318; 319; 320; 321; 322; 323; 324; 325; 326; 327; 328; 329; 330; 331; 332; 333; 334; 335; 336; 337; 338; 339; 340; 341; 342; 343; 344; 345; 346; 347; 348; 349; 350; 351; 352; 353; 354; 355; 356; 357; 358; 359; 360; 361; 362; 363; 364; 365; 366; 367; 368; 369; 370; 371; 372; 373; 374; 375; 376; 377; 378; 379; 380; 381; 382; 383; 384; 385; 386; 387; 388; 389; 390; 391; 392; 393; 394; 395; 396; 397; 398; 399 or 400 nucleotides.

According to the methods of the invention, specific group of single stranded DNA fragments can be a group of fragments having a length inferior or superior to 160 nucleotides (or inferior or superior to the peak as defined above), a group of fragments having a length between 165 and 250 nucleotides, between 145 and 165 nucleotides, between 30 and 120 nucleotides, between 100 and 145 nucleotides; between 165 and 250 nucleotides, between 145 and 250, and 300 and 350 nucleotides.

As used herein, the term "cancer" has its general meaning in the art and includes, but is not limited to, solid tumors and blood borne tumors. The term cancer includes diseases of the skin, tissues, organs, bone, cartilage, blood and vessels. The term "cancer" further encompasses both primary and metastatic cancers. Examples of cancers include, but are not limited to, cancer cells from the bladder, blood, bone, bone marrow, brain, breast, colon, esophagus, gastrointestine, gum, head, kidney, liver, lung, nasopharynx, neck, ovary, prostate, skin, stomach, testis, tongue, or uterus. In addition, the cancer may specifically be of the following histological type, though it is not limited to these: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous; adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; and roblastoma, malignant; Sertoli cell carcinoma; leydig cell tumor, malignant; lipid cell tumor, malignant; paraganglioma, malignant; extramammary paraganglioma, malignant; pheochromocytoma; glomangiosarcoma; malignant melanoma; amelanotic melanoma; superficial spreading melanoma; malig melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyo sarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; Hodgkin's disease; Hodgkin's lymphoma; paragranuloma; malignant lymphoma, small lymphocytic; malignant lymphoma, large cell, diffuse; malignant lymphoma, follicular; mycosis fungoides; other specified non-Hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; and hairy cell leukemia. In some embodiments, the subject suffers from a colorectal cancer, more particularly a metastatic colorectal cancer.

According to the methods of the invention, the cell free nucleic acids are cell free DNA (cfDNA) or circulating cell free DNA (ccfDNA).

According to the methods of the invention, the level of the single stranded DNA fragments of the level of group of single stranded DNA fragments can be made by Q-PCR based method or by sequencing methods. Particularly, the sequencing methods are based on a single stranded DNA library preparation.

According to the invention, the single stranded DNA fragments, can be from a group of genes, same gene or the same exon.

According to the invention, the single stranded DNA fragments allow a discrimination between all the chromosomes in respect to cancer or healthy status, and particularly the chromosomes 1, 4, 5, 6 8, 9, 10, 13, 18, 20, X and Y.

In a particular embodiment, the screening method according to the invention can be done with single stranded DNA obtained from different chromosome like the chromosomes 1, 4, 5, 6 8, 9, 10, 13, X and 20.

According to the invention, the single stranded DNA fragments can be a nuclear or a mitochondrial DNA.

According to the invention, to amplify the single stranded DNA fragments, 1 set of 3 primers can be used.

As used herein, the term "primer" refers to an oligonucleotide, whether occurring naturally as in a purified restriction digest or produced synthetically, which is capable of acting as a point of initiation of nucleic acid sequence synthesis when placed under conditions in which synthesis of a primer extension product which is complementary to a nucleic acid strand is induced, i.e. in the presence of different nucleotide triphosphates and a polymerase in an appropriate buffer ("buffer" includes pH, ionic strength, cofactors etc.) and at a suitable temperature. Typically, a primer has a length of 10; 11; 12; 13; 14; 15; 16; 17; 18; 19; 20; 21; 22; 23; 24; 25; 26; 27; 28; 29; or 30 nucleotides. One or more of the nucleotides of the primer can be modified for instance by addition of a methyl group, a biotin or digoxigenin moiety, a fluorescent tag or by using radioactive nucleotides. A primer sequence need not reflect the exact sequence of the template. For example, a non-complementary nucleotide fragment may be attached to the 5' end of the primer, with the remainder of the primer sequence being substantially complementary to the strand. Primers are typically labelled with a detectable molecule or substance, such as a fluorescent molecule, a radioactive molecule or any others labels known in the art. Labels are known in the art that generally provide (either directly or indirectly) a signal. The term "labelled" is intended to encompass direct labelling of the probe and primers by coupling (i.e., physically linking) a detectable substance as well as indirect labeling by reactivity with another reagent that is directly labeled. Examples of detectable substances include but are not limited to radioactive agents or a fluorophore (e.g. fluorescein isothiocyanate (FITC) or phycoerythrin (PE) or Indocyanine (Cy5)).

Quantitative PCR (QPCR)

The template nucleic acid need not be purified. Nucleic acids may be extracted from a sample by routine techniques such as those described in Diagnostic Molecular Microbiology: Principles and Applications (Persing et al. (eds), 1993, American Society for Microbiology, Washington D.C.).

U.S. Pat. Nos. 4,683,202, 4,683,195, 4,800,159, and 4,965,188 disclose conventional PCR techniques. PCR typically employs two oligonucleotide primers that bind to a selected target nucleic acid sequence. Primers useful in the present invention include oligonucleotides capable of acting as a point of initiation of nucleic acid synthesis within the target nucleic acid sequence. A primer can be purified from a restriction digest by conventional methods, or it can be produced synthetically. If the template nucleic acid is double-stranded (e.g. DNA), it is necessary to separate the two strands before it can be used as a template in PCR. Strand separation can be accomplished by any suitable denaturing method including physical, chemical or enzymatic means. One method of separating the nucleic acid strands involves heating the nucleic acid until it is predominately denatured (e.g., greater than 50%, 60%, 70%, 80%, 90% or 95% denatured). The heating conditions necessary for denaturing template nucleic acid will depend, e.g., on the buffer salt concentration and the length and nucleotide composition of the nucleic acids being denatured, but typically range from about 90° C. to about 105° C. for a time depending on features of the reaction such as temperature and the nucleic acid length. Denaturation is typically performed for about 30 sec to 4 min (e.g., 1 min to 2 min 30 sec, or 1.5 min). If the double-stranded template nucleic acid is denatured by heat, the reaction mixture is allowed to cool to a temperature that promotes annealing of each primer to its target sequence on the target nucleic acid sequence. The temperature for annealing is usually from about 35° C. to about 65° C. (e.g., about 40° C. to about 60° C.; about 45° C. to about 50° C.). Annealing times can be from about 10 sec to about 1 min (e.g., about 20 sec to about 50 sec; about 30 sec to about 40 sec). The reaction mixture is then adjusted to a temperature at which the activity of the polymerase is promoted or optimized, i.e., a temperature sufficient for extension to occur from the annealed primer to generate products complementary to the template nucleic acid. The temperature should be sufficient to synthesize an extension product from each primer that is annealed to a nucleic acid template, but should not be so high as to denature an extension product from its complementary template (e.g., the temperature for extension generally ranges from about 40° C. to about 80° C. (e.g., about 50° C. to about 70° C.; about 60° C.). Extension times can be from about 10 sec to about 5 min (e.g., about 30 sec to about 4 min; about 1 min to about 3 min; about 1 min 30 sec to about 2 min).

QPCR involves use of a thermostable polymerase. The term "thermostable polymerase" refers to a polymerase enzyme that is heat stable, i.e., the enzyme catalyzes the formation of primer extension products complementary to a template and does not irreversibly denature when subjected to the elevated temperatures for the time necessary to effect denaturation of double-stranded template nucleic acids. Generally, the synthesis is initiated at the 3' end of each primer and proceeds in the 5' to 3' direction along the template strand. Thermostable polymerases have been isolated from *Thermus flavus, T. ruber, T. thermophilus, T. aquaticus, T. lacteus, T. rubens, Bacillus stearothermophilus*, and *Methanothermus fervidus*. Nonetheless, polymerases that are not thermostable also can be employed in PCR assays provided the enzyme is replenished. Typically, the polymerase is a Taq polymerase (i.e. *Thermus aquaticus* polymerase).

The primers are combined with PCR reagents under reaction conditions that induce primer extension. Typically, chain extension reactions generally include 50 mM KCl, 10 mM Tris-HCl (pH 8.3), 15 mM MgCl2, 0.001% (w/v) gelatin, 0.5-1.0 µg denatured template DNA, 50 pmoles of each oligonucleotide primer, 2.5 U of Taq polymerase, and 10% DMSO). The reactions usually contain 150 to 320 µM each of dATP, dCTP, dTTP, dGTP, or one or more analogs thereof.

The newly synthesized strands form a double-stranded molecule that can be used in the succeeding steps of the reaction. The steps of strand separation, annealing, and elongation can be repeated as often as needed to produce the desired quantity of amplification products corresponding to the target nucleic acid sequence molecule. The limiting factors in the reaction are the amounts of primers, thermostable enzyme, and nucleoside triphosphates present in the reaction. The cycling steps (i.e., denaturation, annealing, and extension) are preferably repeated at least once. For use in detection, the number of cycling steps will depend, e.g., on the nature of the sample. If the sample is a complex mixture of nucleic acids, more cycling steps will be required to amplify the target sequence sufficient for detection. Generally, the cycling steps are repeated at least about 20 times, but may be repeated as many as 40, 60, or even 100 times.

Quantitative PCR is typically carried out in a thermal cycler with the capacity to illuminate each sample with a beam of light of a specified wavelength and detect the fluorescence emitted by the excited fluorophore. The thermal cycler is also able to rapidly heat and chill samples, thereby taking advantage of the physicochemical properties of the nucleic acids and thermal polymerase.

In order to detect and measure the amount of amplicon (i.e. amplified target nucleic acid sequence) in the sample, a measurable signal has to be generated, which is proportional to the amount of amplified product. All current detection systems use fluorescent technologies. Some of them are non-specific techniques, and consequently only allow the detection of one target at a time. Alternatively, specific detection chemistries can distinguish between non-specific amplification and target amplification. These specific techniques can be used to multiplex the assay, i.e. detecting several different targets in the same assay.

SYBR® Green I: SYBR® Green I is the most commonly used dye for non-specific detection. It is a double-stranded DNA intercalating dye, that fluoresces once bound to the DNA. A pair of specific primers is required to amplify the target with this chemistry. The amount of dye incorporated is proportional to the amount of generated target. The dye emits at 520 nm and fluorescence emitted can be detected and related to the amount of target. The inconvenience of this technique is that the SYBR® Green I will bind to any amplified dsDNA. Consequently, primer dimers or unspecific products introduce a bias in the quantification. However, it is still possible to check for the specificity of the system by running a meltcurve at the end of the PCR run. The principle is that every product has a different dissociation temperature, depending of the size and base contents, so it is still possible to check the number of products amplified. A valid SYBR® assay—primer pair—should produce a unique, well defined peak on the meltcurve. For these reasons, SYBR® Green I is rarely used for qualitative PCR. However, SYBR® Green I is often used as the first step to optimize a specific detection system assay, to check the specificity of the primers and validate the design.

High Resolution Melting dyes (HRM dyes): High Resolution Meltcurve analysis is a newly emerging technology, which characterizes nucleic acid samples based on their dissociation behaviour. It combines the principle of intercalating dyes, meltcurve analyses and the application of specific statistical analyses. HRM uses the fundamental property of the separation of the two strands of DNA with heat (melting), and the monitoring of this melting with a fluorescent dye. On the contrary of SYBR Green, HRM dyes do not inhibit PCR at high concentration. The dye can consequently saturate the amplified target dsDNA and fluoresces. Melting temperature of a dsDNA target depends on GC content, length, and sequence. Due to the high sensitivity of HRM dyes, even a single base change will induce differences in the melting curve, and consequently in fluorescence (Erali M. et al., 2008). This emerging method is less expensive and as precise than probe-based methods. Only a few thermocyclers on the market currently allow the use of this technology, among them the Roche LightCycler®480, the Corbett Life Science Rotor-Gene™ 6000, and the ABI Prism®7500. The main HRM dyes available are EvaGreen, LCGreen®, SYTO® 9 and BEBO.

TaqMan® probes=Double-Dye probes: TaqMan® probes, also called Double-Dye Oligonucleotides, Double-Dye Probes, or Dual-Labelled probes, are the most widely used type of probes and are often the method of choice for scientists who have just started using Real-Time PCR. They were developed by Roche (Basel, Switzerland) and ABI (Foster City, USA) from an assay that originally used a radio-labelled probe (Holland et al. 1991), which consisted of a single-stranded probe sequence that was complementary to one of the strands of the amplicon. A fluorophore is attached to the 5' end of the probe and a quencher to the 3' end. The fluorophore is excited by the machine and passes its energy, via FRET (Fluorescence Resonance Energy Transfer) to the quencher. Traditionally the FRET pair has been FAM as the fluorophore and TAMRA as the quencher. In a well designed probe, FAM does not fluoresce as it passes its energy onto TAMRA. As TAMRA fluorescence is detected at a different wavelength to FAM, the background level of FAM is low. The probe binds to the amplicon during each annealing step of the PCR. When the Taq polymerase extends from the primer which is bound to the amplicon, it displaces the 5' end of the probe, which is then degraded by the 5'-3' exonuclease activity of the Taq polymerase. Cleavage continues until the remaining probe melts off the amplicon. This process releases the fluorophore and quencher into solution, spatially separating them (compared to when they were held together by the probe). This leads to an irreversible increase in fluorescence from the FAM and a decrease in the TAMRA.

LNA® Double-Dye probes: LNA® (Locked Nucleic Acid) was developed by Exiqon® (Vedbaek, Denmark). LNA® changes the conformation of the helix and increases the stability of the duplex. The integration of LNA® bases into Double-Dye Oligonucleotide probes, opens up great opportunities to improve techniques requiring high affinity probes as specific as possible, like SNP detection, expression profiling and in situ hybridization. LNA® is a bicyclic RNA analogue, in which the ribose moiety in the sugar-phosphate backbone is structurally constrained by a methylene bridge between the 2'-oxygen and the 4'-carbon atoms. The integration of LNA® bases into probes changes the conformation of the double helix from the B to A type (Ivanova A. et al., 2007). LNA® conformation allows a much better stacking and therefore a higher stability. By increasing the stability of the duplex, the integration of LNA® monomers into the oligonucleotide sequence allows an increase of the melting Temperature (Tm) of the duplex. It is therefore possible to reduce the size of the probe, which increases the specificity of the probe and helps designing it (Karkare S. et al., 2006).

Molecular Beacon probes: Molecular Beacons are probes that contain a stem-loop structure, with a fluorophore and a quencher at their 5' and 3' ends, respectively. The stem is usually 6 bases long, should mainly consist of C's and G's, and holds the probe in the hairpin configuration (Li Y. et al., 2008). The 'stem' sequence keeps the fluorophore and the quencher in close vicinity, but only in the absence of a sequence complementary to the 'loop' sequence. As long as the fluorophore and the quencher are in close proximity, the quencher absorbs any photons emitted by the fluorophore. This phenomenon is called collisional (or proximal) quenching. In the presence of a complementary sequence, the Beacon unfolds and hybridizes to the target, the fluorophore is then displaced from the quencher, so that it can no longer absorb the photons emitted by the fluorophore, and the probe starts to fluoresce. The amount of signal is proportional to the amount of target sequence, and is measured in real time to allow quantification of the amount of target sequence (Takacs T. et al., 2008). The increase in fluorescence that occurs is reversible, (unlike TaqMan® probes), as there is no cleavage of the probe, that can close back into the hairpin structure at low temperature. The stem structure adds specificity to this type of probe, because the hybrid formed between the probe and target has to be stronger than the intramolecular stem association. Good design of Molecular Beacons can give good results, however the signal can be poor, as no physical separation of fluorophore from quencher occurs. Wavelength-Shifting Molecular Beacons are brighter than standard Molecular Beacons due to an enhanced fluorescence intensity of the emitter fluorophore. These probes contain a harvester fluorophore that absorbs strongly in the wavelength range of the monochromatic light source, an emitter fluorophore of the desired emission color, and a non-fluorescent (dark) quencher. In the absence of complementary nucleic acid targets, the probes are non-fluorescent, whereas in the presence of targets, they fluoresce, not in the emission range of the harvester fluorophore, that absorbs the light, but rather in the emission range of the emitter fluorophore. This shift in emission spectrum is due to the transfer of the absorbed energy from the harvester fluorophore to the emitter fluorophore by FRET, which only takes place in probes that are bound to the targets. Wavelength-Shifting Molecular Beacons are substantially brighter than conventional Molecular Beacons that cannot efficiently absorb energy from the available monochromatic light source (Tyagi S. et al., 2000).

Scorpions® primers: Scorpions® primers are suitable for both quantitative Real-Time PCR and genotyping/end-point analysis of specific DNA targets. They are PCR primers with a "stem-loop" tail consisting of a specific probe sequence, a fluorophore and a quencher. The "stem-loop" tail is separated from the PCR primer sequence by a "PCR blocker", a chemical modification that prevents the Taq polymerase from copying the stem loop sequence of the Scorpions® primer. Such read-through would lead to non-specific opening of the loop, causing a non-specific fluorescent signal. The hairpin loop is linked to the 5' end of a primer via a PCR blocker. After extension of the primer during PCR amplification, the specific probe sequence is able to bind to its complement within the same strand of DNA. This hybridization event opens the hairpin loop so that fluorescence is no longer quenched and an increase in signal is observed. Unimolecular probing is kinetically favorable and highly efficient. Covalent attachment of the probe to the target amplicon ensures that each probe has a target in the near vicinity. Enzymatic cleavage is not required, thereby reducing the time needed for signaling compared to TaqMan® probes, which must bind and be cleaved before an increase in fluorescence is observed. There are three types of Scorpions® primers. Standard Scorpions®, which consist of a bi-labelled probe with a fluorescent dye at the 5' end and an internal non-fluorescent quencher. FRET Scorpions®, for use on a LightCycler® system. As the capillary system will only excite at 470 nm (FAM absorption wavelength) it is necessary to incorporate a FAM within the stem. A ROX is placed at the 5'end of the Scorpions® primer, FAM is excited and passes its energy onto the ROX. Duplex Scorpions® have also been developed to give much better signal intensity than the normal Scorpions® format. In Standard Scorpions® the quencher and fluorophore remain within the same strand of DNA and some quenching can occur even in the open form. In the Duplex Scorpions® the quencher is on a different oligonucleotide and physical separation between the quencher and fluorophore is greatly increased, reducing the quenching when the probe is bound to the target.

Hybridization probes (also called FRET probes): Roche has developed hybridization probes (Caplin et al. 1999) for use with their LightCycler®. Two probes are designed to bind adjacent to one another on the amplicon. One has a 3' label of FAM, whilst the other has a 5' LC dye, LC red 640 or 705. When the probes are not bound to the target sequence, the fluorescent signal from the reporter dye is not detected. However, when the probes hybridize to the target sequence during the PCR annealing step, the close proximity of the two fluorophores allows energy transfer from the donor to the acceptor dye, resulting in a fluorescent signal that is detected.

TaqMan® MGB® probes: TaqMan® MGB® probes have been developed by Epoch Biosciences (Bothell, USA) and Applied Biosystems (Foster City, USA). They bind to the minor groove of the DNA helix with strong specificity and affinity. When the TaqMan® MGB® probe is complemented with DNA, it forms a very stable duplex with DNA. The probe carries the MGB® moiety at the 3' end. The MGB strongly increases the probe Tm, allowing shorter, hence more specific designs. The probe performs particularly well with A/T rich regions, and is very successful for SNP detection (Walburger et al., 2001). It can also be a good alternative when trying to design a probe which should be located in the splice junction (for which conventional probes are hard to design). Smaller probes can be designed with Tm as 65-67° C., which gives a better discrimination (the probe is more specific for single mismatch). A good alternative to MGB probes are LNA® probes where the increase in Tm induced by the addition of LNA® bases is specific, contrary to the MGB moeity (cf. p. 15). During the primer extension step, the hybridized probe is cleaved by the 5' exonuclease activity of Taq polymerase and an increase in fluorescence is seen. Fluorescence of the cleaved probe during PCR is monitored in Real-Time by the thermocycler.

MGB Eclipse® probes: MGB Eclipse® probes also known as QuantiProbes, have originally been developed by Epoch Biosciences (Bothell, USA). MGB Eclipse® probes carry a minor groove binder moiety that allows the use of short probes for very high specificity. These are short linear probes that have a minor groove binder and a quencher on the 5' end and a fluorophore on the 3' end. This is the opposite orientation to TaqMan® MGB® probes and it is thought that the minor groove binder prevents the exonuclease activity of the Taq polymerase from cleaving the probe. The quencher is a Non Fluorescent Quencher also known as Eclipse Dark Quencher. Quenching occurs when the random coiling of the probe in the free form brings the quencher and the fluorophore close to another. The probe is straightened out when bound to its target and quenching is decreased, leading to an increase in fluorescent signal. The technologies that have been discussed above are the most widely used today, but numerous other technologies have occurred in publications, or are available on the market, such as: Resonsense probes, Light-up probes, HyBeacon® probes, LUX primers, Yin-yang probes, or Amplifluor®. You can contact us for more information on any of them.

The majority of the thermocyclers on the market now offer similar characteristics. Typically, thermocyclers involve a format of glass capillaries, plastics tubes, 96-well plates or 384-wells plates. The thermocylcer also involve a software analysis.

Typically quantitative PCR involves use of:
Taq polymerase: A HotStart Taq polymerase is inactive at low temperatures (room temperature). Heating at 95° C. for several—usually 5 to 10—minutes activates the enzyme, and the amplification can begin once the primers are annealed. The enzyme is not active until the entire DNA is denatured. Two major HotStart modifications exist, the antibody-blocked Taq and the chemically-blocked Taq. The antibody-blocked Taq is inactive because it is bound to a thermolabile inhibitor that is denatured during the initial step of PCR. The chemically-blocked Taq provides one clear advantage over the antibody-blocked Taq, as it is completely inactive at 60° C., (the hybridization temperature of primers), thus preventing the formation of non-specific amplification and reducing primer dimer formation.

dNTps/dUTps: Some kits contain a blend of dNTPs and dUTPs, other ones contain only dNTPs. Using only dNTPs increases the sensitivity, the reason being that the Taq incorporates more easily dNTPs than dUTPs. However, using a mix containing dUTPs brings security to the assay, in case of contamination from a previous PCR product. Thanks to the UNG activity in association with incorporated dUTPs, this contamination can be eliminated.

Uracil-N-Glycosylase: The Uracil-N-Glycosylase is an enzyme that hydrolyses all single-stranded and double-stranded DNA containing dUTPs. Consequently, if all PCR amplifications are performed in the presence of a dNTPs/dUTPs blend, by carrying a UNG step before every run it is possible to get rid of any previous PCR product.

ROX reference dye: Some thermocyclers require Master-Mix containing ROX dye for normalization. This is the case for the ABI and Eppendorf machines, and optional on the Stratagene machines. If you work with such machines, it is easier to work with the ROX dye already incorporated in the MasterMix rather than adding it manually. It guarantees a higher level of reproducibility and homogeneity of your assays.

Fluorescein: For iCycler iQ®, My iQ® and iQ5 machines (BioRad thermocyclers), the normalization method for SYBR® Green assay uses Fluorescein to create a "virtual background". As in the case for the ROX, it is better and easier to use a MasterMix that contains pre-diluted Fluorescein, guaranteeing higher reproducibility and homogeneity of your assays.

$MgCl_2$: $MgCl_2$ is necessary for the Taq activity. MgCl concentration in MasterMixes is optimized according to the amount of Taq and also the buffer composition. However, it may be necessary sometimes to add MgCl2 and most MasterMixes include an additional tube of MgCl2.

Inert colored dye: Some buffers also include an inert colored dye, to enable visualization of the buffer when loading in the wells. This colored dye has no effect on the sensitivity of the assay and is a convenient working tool. Note that such mixes, in combination with white plastic plates, provide better levels of fluorescence and a really easy way of working.

Well-designed primers and probes are a prerequisite for successful quantitative PCR. By using well-designed primers and probes, PCR efficiencies of 100% can be obtained. Typically primers are designed using a design software (for example Oligo® Primer Analysis Software). Most thermocycler softwares now offer tools to help in designing primers with the best characteristics. Some of the best softwares are Beacon Designer, Primer Express, and DNA Star . . . . Some other tools are freely available on the web, for example:

http://medgen.ugent.be/rtprimerdb/ (human primer and probe database)
http://frontend.bioinfo.rpi.edu/applications/mfold/ (for testing secondary structures)
http://www.ebi.ac.uk/~lenov/meltinghome.html (Tm calculators)
http://frodo.wi.mit.edu/cgi-bin/primer/primer3_www.cgi
http://bibiserv.techfak.uni-bielefeld.de/genefisher2
http://www.premierbiosoft.com/qpcr/index Typically, Q PCR involves the preparation of a standard curve for each amplified target nucleic acid sequence. Preparing a standard curve can indeed provide a good idea of the performance of the qPCR and thus serves as a quality control. The standard curve should cover the complete range of expected expression. Using standard material the standard curve should include at least 5 points of dilution, each of them in duplicate (at least). The 10-fold or 2-fold dilution range should cover the largest range of expression levels. Plotting these points on a standard curve, will determine the linearity, the efficiency, the sensitivity and the reproducibility of the assay. According to the present invention the standard curve is prepared from a genomic DNA sample. As used herein, "genomic DNA sample" or "gDNA" refers to a genomic DNA sample prepared from a DNA preparation. Methods for DNA purification are well known in the art. The genomic DNA may be prepared from a cell that is of the same organism than the cell that is used for preparing the nucleic acid sample of the invention (i.e. a human cell). Furthermore the cell from which the genomic sample is prepared must present the same ploidy than the cell used for preparing the nucleic acid sample of the invention; i.e. the cells present the same chromosomal abnormalities (e.g. in case of cancer cells). Typically, the genomic DNA sample is prepared from a cell for which the DII as defined above is about 1.

Sequencing Methods

Direct sequencing may be accomplished by any method, including without limitation chemical sequencing, using the Maxam-Gilbert method (Methods in Enzymology 65, 499-560 (1980)); by enzymatic sequencing, using the Sanger method Proc. Natl. Acad. Sci. USA 74, 5463-67 (1977)).; mass spectrometry sequencing; sequencing using a chip-based technology; and real-time quantitative PCR.

In the chemical sequencing, base specific modifications result in a base specific cleavage of the radioactive or fluorescently labeled DNA fragment. With the four separate base specific cleavage reactions, four sets of nested fragments are produced which are separated according to length by polyacrylamide gel electrophoresis (PAGE). After autoradiography, the sequence can be read directly since each band (fragment) in the gel originates from a base specific cleavage event. Thus, the fragment lengths in the four "ladders" directly translate into a specific position in the DNA sequence.

In the enzymatic sequencing, the four base specific sets of DNA fragments are formed by starting with a primer/template system elongating the primer into the unknown DNA sequence area and thereby copying the template and synthesizing a complementary strand by DNA polymerases, such as Klenow fragment of *E. coli* DNA polymerase I, a DNA polymerase from *Thermus aquaticus*, Taq DNA polymerase, or a modified T7 DNA polymerase, Sequenase (Tabor et al., Proc. Natl. Acad. Scl. USA 84, 4767-4771 (1987)), in the presence of chain-terminating reagents.

Several new methods for DNA sequencing (High-throughput sequencing (HTS) methods) were developed in the mid to late 1990s and were implemented in commercial DNA sequencers by the year 2000. Together these were called the "next-generation" or "second-generation" sequencing methods. These HTS included but are not limited to: Single-molecule real-time sequencing, Ion semiconductor, Pyrosequencing, Sequencing by synthesis, Sequencing by ligation, Nanopore Sequencing, Chain termination and Sequencing by hybridization. Some of these methods allow a Whole Gene Sequencing (WGS), Whole Exome Sequencing (WES) or a Targeted Sequencing.

Double strand library preparation (DSP) is used typically for cell-free DNA analysis for several reasons: it is an easy protocol to carry out in the laboratory as it takes only a few hours compared to single strand library preparation protocols, which typically take much longer; it is cheap on a per-sample basis; and a lot of optimization has been done on double strand library preparation so that it is more efficient and has less adapter ligation bias (21). Single strand library preparation (SSP) was recently designed to bypass the limits of the conventional DNA library in order to recover damaged and short double strand DNA fragments, especially in the paleontology field (21,22). High-throughput sequencing of cfDNA from SSP (SSP-S) has been used only by Snyder et al. (23) and Burnham et al. (24 & 25).

SSP-S offers various advantages over DSP-S with regard to the detection of cfDNA. The most important reason seem to be that fragments that are damaged, for example with nicks or abasic sites, are likely to be lost during DSP, but are retained during SSP, so if a sample has DNA damage (e.g. cfDNA), SSP is likely to capture the damaged molecules. DNA molecules with single-strand breaks on one or both strands may be present in cfDNA. Whereas such molecules are completely lost under DSP procedure, SSP results to DNA break down into several fragments during heat denaturation and each fragment has an independent chance of being recovered in the library. Consequently, SSP libraries may contain a larger fraction of shorter molecules than those produced by the double strand method as demonstrated by Bennett et al. SSP-S appears better suited than conventional DSP-S when optimal recovery of cfDNA is required for its analysis. However never in the literature SSP-S was used to discriminate healthy subject with cancer patients according to the claims.

Predetermined Corresponding Reference Values

Typically, the predetermined corresponding reference value can be relative to a number or value derived from population studies, including without limitation, subjects of the same or similar age range, subjects in the same or similar ethnic group, subjects at risk of cancer, subjects having the same severity of cancer and subject without cancer (healthy subject). Such predetermined corresponding reference values can be derived from statistical analyses and/or risk prediction data of populations obtained from mathematical algorithms and computed indices of the disease.

Typically, the predetermined corresponding reference value is a threshold value or a cut-off value. A "threshold value" or "cut-off value" can be determined experimentally, empirically, or theoretically. A threshold value can also be arbitrarily selected based upon the existing experimental and/or clinical conditions, as would be recognized by a person of ordinary skilled in the art. For example, retrospective measurement of the expression level of the marker of interest (e.g. single stranded DNA fragments for a specific length, ratio between single stranded DNA fragments for a specific length or between group of single stranded DNA fragments for a specific length) in properly banked historical subject samples may be used in establishing the predetermined corresponding reference value. In some embodiments, the predetermined corresponding reference value is the median measured in the population of the subjects for the marker of interest (e.g. single stranded DNA fragments for a specific length, ratio between single stranded DNA fragments for a specific length or between group of single stranded DNA fragments for a specific length). In some embodiments, the threshold value has to be determined in order to obtain the optimal sensitivity and specificity according to the function of the test and the benefit/risk balance (clinical consequences of false positive and false negative). Typically, the optimal sensitivity and specificity (and so the threshold value) can be determined using a Receiver Operating Characteristic (ROC) curve based on experimental data. For example, after determining the expression level of the marker of interest (e.g. single stranded DNA fragments for a specific length, ratio between single stranded DNA fragments for a specific length or between group of single stranded DNA fragments for a specific length) in a group of reference, one can use algorithmic analysis for the statistic treatment of the expression levels determined in samples to be tested, and thus obtain a classification standard having significance for sample classification. The full name of ROC curve is receiver operator characteristic curve, which is also known as receiver operation characteristic curve. It is mainly used for clinical biochemical diagnostic tests. ROC curve is a comprehensive indicator the reflects the continuous variables of true positive rate (sensitivity) and false positive rate (1-specificity). It reveals the relationship between sensitivity and specificity with the image composition method. A series of different cut-off values (thresholds or critical values, boundary values between normal and abnormal results of diagnostic test) are set as continuous variables to calculate a series of sensitivity and specificity values. Then sensitivity is used as the vertical coordinate and specificity is used as the horizontal coordinate to draw a curve. The higher the area under the curve (AUC), the higher the accuracy of diagnosis. On the ROC curve, the point closest to the far upper left of the coordinate diagram is a critical point having both high sensitivity and high specificity values. The AUC value of the ROC curve is between 1.0 and 0.5. When AUC>0.5, the diagnostic result gets better and better as AUC approaches 1. When AUC is between 0.5 and 0.7, the accuracy is low. When AUC is between 0.7 and 0.9, the accuracy is moderate. When AUC is higher than 0.9, the accuracy is quite high. This algorithmic method is preferably done with a computer. Existing software or systems in the art may be used for the drawing of the ROC curve, such as: MedCalc 9.2.0.1 medical statistical software, SPSS 9.0, ROCPOWER.SAS, DESIGNROC.FOR, MULTIREADER POWER.SAS, CREATE-ROC.SAS, GB STAT VI0.0 (Dynamic Microsystems, Inc. Silver Spring, Md., USA), etc.

In some embodiments, the predetermined corresponding reference value is typically determined by carrying out a method comprising the steps of:
 a) providing a collection of samples from subjects;
 b) providing, for each sample provided at step a), information relating to the actual clinical profile of the subject (healthy or suffering from a cancer);
 c) providing a serial of arbitrary quantification values;
 d) determining the level of the marker of interest (e.g. single stranded DNA fragments for a specific length, ratio between single stranded DNA fragments for a specific length or between group of single stranded DNA fragments for a specific length) for each sample contained in the collection provided at step a);
 e) classifying said blood samples in two groups for one specific arbitrary quantification value provided at step c), respectively: (i) a first group comprising samples that exhibit a quantification value for level that is lower than the said arbitrary quantification value contained in the said serial of quantification values; (ii) a second group comprising samples that exhibit a quantification value for said level that is higher than the said arbitrary quantification value contained in the said serial of quantification values; whereby two groups of samples are obtained for the said specific quantification value, wherein the samples of each group are separately enumerated;

f) calculating the statistical significance between (i) the quantification value obtained at step e) and (ii) the actual clinical profile of the subjects from which samples contained in the first and second groups defined at step f) derive;

g) reiterating steps f) and g) until every arbitrary quantification value provided at step d) is tested;

h) setting the said predetermined corresponding reference value as consisting of the arbitrary quantification value for which the highest statistical significance (most significant) has been calculated at step g).

Thus in some embodiments, the predetermined corresponding reference value thus allows discrimination between healthy subject and subjects suffering from cancer. Practically, high statistical significance values (e.g. low P values) are generally obtained for a range of successive arbitrary quantification values, and not only for a single arbitrary quantification value. Thus, in one alternative embodiment of the invention, instead of using a definite predetermined corresponding reference value, a range of values is provided. Therefore, a minimal statistical significance value (minimal threshold of significance, e.g. maximal threshold P value) is arbitrarily set and a range of a plurality of arbitrary quantification values for which the statistical significance value calculated at step g) is higher (more significant, e.g. lower P value) are retained, so that a range of quantification values is provided. This range of quantification values includes a "cut-off" value as described above. For example, according to this specific embodiment of a "cut-off" value, the diagnosis can be determined by comparing the level of the marker of interest (e.g. single stranded DNA fragments for a specific length, ratio between single stranded DNA fragments for a specific length or between group of single stranded DNA fragments for a specific length) with the range of values which are identified. In certain embodiments, a cut-off value thus consists of a range of quantification values, e.g. centered on the quantification value for which the highest statistical significance value is found (e.g. generally the minimum p value which is found). For example, on a hypothetical scale of 1 to 10, if the ideal cut-off value (the value with the highest statistical significance) is 5, a suitable (exemplary) range may be from 4-6. Therefore, a subject may be assessed by comparing values obtained by measuring the level of the marker of interest (e.g. single stranded DNA fragments for a specific length, ratio between single stranded DNA fragments for a specific length or between group of single stranded DNA fragments for a specific length), where values higher (or lower depending on the selected marker) than 5 reveal that the subject suffers from cancer and values lower (or higher depending on the selected marker) than 5 reveal that the subject does not suffer from a cancer. In some embodiments, a subject may be screened for a cancer by comparing values obtained by measuring the level of the marker of interest (e.g. single stranded DNA fragments for a specific length, ratio between single stranded DNA fragments for a specific length or between group of single stranded DNA fragments for a specific length) and comparing the values on a scale, where values above (or below depending on the selected marker) the range of 4-6 indicate that the subject suffers from a cancer and values below or above depending on the selected marker) the range of 4-6 indicate that the subject does not suffer from a cancer, with values falling within the range of 4-6 indicate that further investigation are needed for determining whether the subject suffers from a cancer.

According to the invention, the variation of the level of the single stranded DNA fragments or the level of a group of single stranded DNA fragments may be evaluated.

For example, when the level of at least one single stranded DNA fragment between 20 and 160 nucleotides or between 240 and 320 nucleotides for a subject suspected to have a cancer is determined, the level of a single stranded DNA fragment of the same size is determined for a healthy subject as reference value. In this case, the subject suspected to have a cancer will be diagnosed to have a cancer if the level of the single stranded DNA fragment of this subject is higher than the level of a healthy subject. Accordingly, if the level of the single stranded DNA fragment of this subject is lower or equal than the level of a healthy subject, the subject suspected to have a cancer will be diagnosed to have no cancer.

In contrary if the single stranded DNA fragment is between 160 and 240 nucleotides or between 320 and 400 nucleotides, the subject suspected to have a cancer will be diagnosed to have a cancer if the level of this subject is lower to the level of a healthy patient. Accordingly, if the level of the single stranded DNA fragment of this subject is higher or equal than the level of a healthy subject, the subject suspected to have a cancer will be diagnosed to have no cancer (see FIG. 1).

When the level of a group of single stranded DNA fragments between 20 and 160 nucleotides or between 240 and 320 nucleotides for a subject suspected to have a cancer is determined, the level of the same group of single stranded DNA fragments of the same size is determined for a healthy subject as reference value. In this case, the subject suspected to have a cancer will be diagnosed to have a cancer if the level of the group of single stranded DNA fragments of this subject is higher to the level of a healthy subject. Accordingly, if the level of the group of single stranded DNA fragments of this subject is lower or equal than the level of a healthy subject, the subject suspected to have a cancer will be diagnosed to have no cancer.

In contrary if the group of single stranded DNA fragment is between 160 and 240 nucleotides or between 320 and 400 nucleotides, the subject suspected to have a cancer will be diagnosed to have a cancer if the level of this subject is lower to the level of a healthy subject. Accordingly, if the level of the group of single stranded DNA fragments of this subject is higher or equal than the level of a healthy subject, the subject suspected to have a cancer will be diagnosed to have no cancer (see FIG. 1).

For example, when the level of at least one single stranded DNA fragment between 20 and 160 nucleotides or between 240 and 320 nucleotides for a subject suspected to have a cancer is determined, the level of a single stranded DNA fragment of the same size is determined for a cancer subject as reference value. In this case, the subject suspected to have a cancer will be diagnosed to have a cancer if the level of the single stranded DNA fragment of this subject is higher or equal than the level of a cancer subject. Accordingly, if the level of the single stranded DNA fragment of this subject is lower than the level of a cancer subject, the subject suspected to have a cancer will be diagnosed to have no cancer.

In contrary if the single stranded DNA fragment is between 160 and 240 nucleotides or between 320 and 400 nucleotides, the subject suspected to have a cancer will be diagnosed to have a cancer if the level of this subject is lower to the level of a cancer patient. Accordingly, if the level of the single stranded DNA fragment of this subject is higher or equal than the level of a cancer subject, the subject suspected to have a cancer will be diagnosed to have no cancer (see FIG. 1).

When the level of a group of single stranded DNA fragments between 20 and 160 nucleotides or between 240 and 320 nucleotides for a subject suspected to have a cancer is determined, the level of the same group of single stranded DNA fragment of the same size is determined for a cancer subject as reference value. In this case, the subject suspected to have a cancer will be diagnosed to have a cancer if the level of the group of single stranded DNA fragments of this subject is higher or equal to the level of a cancer subject (as reference). Accordingly, if the level of the group of single stranded DNA fragments of this subject is lower than the level of a cancer subject, the subject suspected to have a cancer will be diagnosed to have no cancer.

In contrary if the group of single stranded DNA fragment is between 160 and 240 nucleotides or between 320 and 400 nucleotides, the subject suspected to have a cancer will be diagnosed to have a cancer if the level of this subject is higher to the level of a cancer subject. Accordingly, if the level of the group of single stranded DNA fragments of this subject is lower or equal than the level of a cancer subject, the subject suspected to have a cancer will be diagnosed to have no cancer (see FIG. 1).

According to the invention, discriminations are globally determined either from proportion (in relation to total fragments) of a single fragment or a fragments group, or from a ratio of two specific sizes of fragments or of a specific size relative to a group of fragments size or of fragments size group with respect to another fragments size group.

Therapeutic Applications

The methods of the present invention can also be suitable for determining whether a subject is eligible or not to an anti-cancer treatment. An anti-cancer treatment typically consists of radiotherapy, chemotherapy, immunotherapy or a combination thereof. The treatment can also consist of an adjuvant therapy (i.e. treatment after chirurgical resection of the primary tumor) of a neoadjuvant therapy (i.e. treatment before chirurgical resection of the primary tumor).

Thus, the invention also relates to a method of treating a cancer in subject identified has having a cancer according to the methods of the invention wherein radiotherapy, chemotherapy, immunotherapy or a combination thereof is used to treat said subject.

In some embodiments, the methods of the present invention are suitable for determining whether a subject is eligible or not to a treatment with a chemotherapeutic agent. For example, when it is concluded that the subject has a cancer then the physician can take the choice to administer the subject with a chemotherapeutic agent.

The term "chemotherapeutic agent" refers to chemical compounds that are effective in inhibiting tumor growth. Examples of chemotherapeutic agents include alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoraramide and trimethylolomelamine; acetogenins (especially bullatacin and bullatacinone); a carnptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CBI-TMI); eleutherobin; pancratistatin; a sarcodictyin; spongistatin; nitrogen mustards such as chlorambucil, chlornaphazine, cholophosphamide, estrarnustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as the enediyne antibiotics (e.g. calicheamicin, especially calicheamicin (11 and calicheamicin 211, see, e.g., Agnew Chem Intl. Ed. Engl. 33:183-186 (1994); dynemicin, including dynemicin A; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycins, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins, mycophenolic acid, nogalarnycin, olivomycins, peplomycin, potfiromycin, puromycin, quelamycin, rodorubicin, streptomgrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophospharnide glycoside; aminolevulinic acid; amsacrine; bestrabucil; bisantrene; edatraxate; defofamine; demecolcine; diaziquone; eflornithine; elliptinium acetate; an epothilone; etoglucid; gallium nitrate; hydroxyurea; lentinan; lonidamine; maytansinoids such as maytansine and ansamitocins; mitoguazone; mitoxantrone; mopidamol; nitracrine; pento statin; phenamet; pirarubicin; podophyllinic acid; 2-ethylhydrazide; procarbazine; PSK®; razoxane; rhizoxin; sizofiran; spirogennanium; tenuazonic acid; triaziquone; 2,2',2"-trichlorotriethylarnine; trichothecenes (especially T-2 toxin, verracurin A, roridinA and anguidine); urethan; vindesine; dacarbazine; mannomustine; mitobromtol; mitolactol; pipobroman; gacytosine; arabinoside ("Ara-C"); cyclophosphamide; thiotepa; taxoids, e.g. paclitaxel (TAXOL®, Bristol-Myers Squibb Oncology, Princeton, N.J.) and doxetaxel (TAXOTERE®, Rhone-Poulenc Rorer, Antony, France); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS 2000; difluoromethylornithine (DMFO); retinoic acid; capecitabine; and pharmaceutically acceptable salts, acids or derivatives of any of the above. Also included in this definition are antihormonal agents that act to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY117018, onapristone, and toremifene (Fareston); and anti-androgens such as flutamide, nilutamide, bicalutamide, leuprolide, and goserelin; and pharmaceutically acceptable salts, acids or derivatives of any of the above.

In some embodiments, the methods of the present invention are suitable for determining whether a subject is eligible or not to targeted therapy. For example, when it is concluded that the subject has a cancer then the physician can take the choice to administer the subject with a targeted therapy.

Targeted cancer therapies are drugs or other substances that block the growth and spread of cancer by interfering with specific molecules ("molecular targets") that are involved in the growth, progression, and spread of cancer. Targeted cancer therapies are sometimes called "molecularly targeted drugs," "molecularly targeted therapies," "precision medicines," or similar names.

In some embodiments, the targeted therapy consists of administering the subject with a tyrosine kinase inhibitor. The term "tyrosine kinase inhibitor" refers to any of a variety of therapeutic agents or drugs that act as selective or non-selective inhibitors of receptor and/or non-receptor tyrosine kinases. Tyrosine kinase inhibitors and related compounds are well known in the art and described in U.S Patent Publication 2007/0254295, which is incorporated by reference herein in its entirety. It will be appreciated by one of skill in the art that a compound related to a tyrosine kinase inhibitor will recapitulate the effect of the tyrosine kinase inhibitor, e.g., the related compound will act on a different member of the tyrosine kinase signaling pathway to produce the same effect as would a tyrosine kinase inhibitor of that tyrosine kinase. Examples of tyrosine kinase inhibitors and related compounds suitable for use in methods of embodiments of the present invention include, but are not limited to, dasatinib (BMS-354825), PP2, BEZ235, saracatinib, gefitinib (Iressa), sunitinib (Sutent; SU11248), erlotinib (Tarceva; OSI-1774), lapatinib (GW572016; GW2016), canertinib (CI 1033), semaxinib (SU5416), vatalanib (PTK787/ZK222584), sorafenib (BAY 43-9006), imatinib (Gleevec; STI571), leflunomide (SU101), vandetanib (Zactima; ZD6474), MK-2206 (8-[4-aminocyclobutyl)phenyl]-9-phenyl-1,2,4-triazolo [3,4-f][1,6] naphthyridin-3(2H)-one hydrochloride) derivatives thereof, analogs thereof, and combinations thereof. Additional tyrosine kinase inhibitors and related compounds suitable for use in the present invention are described in, for example, U.S Patent Publication 2007/0254295, U.S. Pat. Nos. 5,618,829, 5,639,757, 5,728,868, 5,804,396, 6,100,254, 6,127,374, 6,245,759, 6,306,874, 6,313,138, 6,316,444, 6,329,380, 6,344,459, 6,420,382, 6,479,512, 6,498,165, 6,544,988, 6,562,818, 6,586,423, 6,586,424, 6,740,665, 6,794,393, 6,875,767, 6,927,293, and 6,958,340, all of which are incorporated by reference herein in their entirety. In certain embodiments, the tyrosine kinase inhibitor is a small molecule kinase inhibitor that has been orally administered and that has been the subject of at least one Phase I clinical trial, more preferably at least one Phase II clinical, even more preferably at least one Phase III clinical trial, and most preferably approved by the FDA for at least one hematological or oncological indication. Examples of such inhibitors include, but are not limited to, Gefitinib, Erlotinib, Lapatinib, Canertinib, BMS-599626 (AC-480), Neratinib, KRN-633, CEP-11981, Imatinib, Nilotinib, Dasatinib, AZM-475271, CP-724714, TAK-165, Sunitinib, Vatalanib, CP-547632, Vandetanib, Bosutinib, Lestaurtinib, Tandutinib, Midostaurin, Enzastaurin, AEE-788, Pazopanib, Axitinib, Motasenib, OSI-930, Cediranib, KRN-951, Dovitinib, Seliciclib, SNS-032, PD-0332991, MKC-I (Ro-317453; R-440), Sorafenib, ABT-869, Brivanib (BMS-582664), SU-14813, Telatinib, SU-6668, (TSU-68), L-21649, MLN-8054, AEW-541, and PD-0325901.

In some embodiments, the methods of the present invention are suitable for determining whether a subject is eligible or not to a treatment with an immunotherapeutic agent. For example, when it is concluded that the subject has a cancer then the physician can take the choice to administer the subject with an immunotherapeutic agent.

The term "immunotherapeutic agent," as used herein, refers to a compound, composition or treatment that indirectly or directly enhances, stimulates or increases the body's immune response against cancer cells and/or that decreases the side effects of other anticancer therapies. Immunotherapy is thus a therapy that directly or indirectly stimulates or enhances the immune system's responses to cancer cells and/or lessens the side effects that may have been caused by other anti-cancer agents. Immunotherapy is also referred to in the art as immunologic therapy, biological therapy biological response modifier therapy and biotherapy. Examples of common immunotherapeutic agents known in the art include, but are not limited to, cytokines, cancer vaccines, monoclonal antibodies and non-cytokine adjuvants. Alternatively the immunotherapeutic treatment may consist of administering the subject with an amount of immune cells (T cells, NK, cells, dendritic cells, B cells . . . ).

Immunotherapeutic agents can be non-specific, i.e. boost the immune system generally so that the human body becomes more effective in fighting the growth and/or spread of cancer cells, or they can be specific, i.e. targeted to the cancer cells themselves immunotherapy regimens may combine the use of non-specific and specific immunotherapeutic agents.

Non-specific immunotherapeutic agents are substances that stimulate or indirectly improve the immune system. Non-specific immunotherapeutic agents have been used alone as a main therapy for the treatment of cancer, as well as in addition to a main therapy, in which case the non-specific immunotherapeutic agent functions as an adjuvant to enhance the effectiveness of other therapies (e.g. cancer vaccines). Non-specific immunotherapeutic agents can also function in this latter context to reduce the side effects of other therapies, for example, bone marrow suppression induced by certain chemotherapeutic agents. Non-specific immunotherapeutic agents can act on key immune system cells and cause secondary responses, such as increased production of cytokines and immunoglobulins. Alternatively, the agents can themselves comprise cytokines. Non-specific immunotherapeutic agents are generally classified as cytokines or non-cytokine adjuvants.

A number of cytokines have found application in the treatment of cancer either as general non-specific immunotherapies designed to boost the immune system, or as adjuvants provided with other therapies. Suitable cytokines include, but are not limited to, interferons, interleukins and colony-stimulating factors.

Interferons (IFNs) contemplated by the present invention include the common types of IFNs, IFN-alpha (IFN-a), IFN-beta (IFN-beta) and IFN-gamma (IFN-y). IFNs can act directly on cancer cells, for example, by slowing their growth, promoting their development into cells with more normal behaviour and/or increasing their production of antigens thus making the cancer cells easier for the immune system to recognise and destroy. IFNs can also act indirectly on cancer cells, for example, by slowing down angiogenesis, boosting the immune system and/or stimulating natural killer (NK) cells, T cells and macrophages. Recombinant IFN-alpha is available commercially as Roferon (Roche Pharmaceuticals) and Intron A (Schering Corporation). The use of IFN-alpha, alone or in combination with other immunotherapeutics or with chemotherapeutics, has shown efficacy in the treatment of various cancers including melanoma (including metastatic melanoma), renal cancer (including metastatic renal cancer), breast cancer, prostate cancer, and cervical cancer (including metastatic cervical cancer).

Interleukins contemplated by the present invention include IL-2, IL-4, IL-11 and IL-12. Examples of commercially available recombinant interleukins include Proleukin® (IL-2; Chiron Corporation) and Neumega® (IL-12; Wyeth Pharmaceuticals). Zymogenetics, Inc. (Seattle, Wash.) is currently testing a recombinant form of IL-21, which is also contemplated for use in the combinations of the present invention. Interleukins, alone or in combination with other immunotherapeutics or with chemotherapeutics, have shown efficacy in the treatment of various cancers including renal cancer (including metastatic renal cancer), melanoma (including metastatic melanoma), ovarian cancer (including recurrent ovarian cancer), cervical cancer (including metastatic cervical cancer), breast cancer, colorectal cancer, lung cancer, brain cancer, and prostate cancer.

Interleukins have also shown good activity in combination with IFN-alpha in the treatment of various cancers (Negrier et al., Ann Oncol. 2002 13(9):1460-8; Tourani et al, J. Clin. Oncol. 2003 21(21):398794).

Colony-stimulating factors (CSFs) contemplated by the present invention include granulocyte colony stimulating factor (G-CSF or filgrastim), granulocyte-macrophage colony stimulating factor (GM-CSF or sargramostim) and erythropoietin (epoetin alfa, darbepoietin). Treatment with one or more growth factors can help to stimulate the generation of new blood cells in subjects undergoing traditional chemotherapy. Accordingly, treatment with CSFs can be helpful in decreasing the side effects associated with chemotherapy and can allow for higher doses of chemotherapeutic agents to be used. Various-recombinant colony stimulating factors are available commercially, for example, Neupogen® (G-CSF; Amgen), Neulasta (pegfilgrastim; Amgen), Leukine (GM-CSF; Berlex), Procrit (erythropoietin; Ortho Biotech), Epogen (erythropoietin; Amgen), Aranesp (erythropoietin). Colony stimulating factors have shown efficacy in the treatment of cancer, including melanoma, colorectal cancer (including metastatic colorectal cancer), and lung cancer.

Non-cytokine adjuvants suitable for use in the combinations of the present invention include, but are not limited to, Levamisole, alum hydroxide (alum), Calmette-Guerin bacillus (ACG), incomplete Freund's Adjuvant (IFA), QS-21, DETOX, Keyhole limpet hemocyanin (KLH) and dinitrophenyl (DNP). Non-cytokine adjuvants in combination with other immuno- and/or chemotherapeutics have demonstrated efficacy against various cancers including, for example, colon cancer and colorectal cancer (Levimasole); melanoma (BCG and QS-21); renal cancer and bladder cancer (BCG).

In addition to having specific or non-specific targets, immunotherapeutic agents can be active, i.e. stimulate the body's own immune response, or they can be passive, i.e. comprise immune system components that were generated external to the body.

Passive specific immunotherapy typically involves the use of one or more monoclonal antibodies that are specific for a particular antigen found on the surface of a cancer cell or that are specific for a particular cell growth factor. Monoclonal antibodies may be used in the treatment of cancer in a number of ways, for example, to enhance a subject's immune response to a specific type of cancer, to interfere with the growth of cancer cells by targeting specific cell growth factors, such as those involved in angiogenesis, or by enhancing the delivery of other anticancer agents to cancer cells when linked or conjugated to agents such as chemotherapeutic agents, radioactive particles or toxins.

Monoclonal antibodies currently used as cancer immunotherapeutic agents that are suitable for inclusion in the combinations of the present invention include, but are not limited to, rituximab (Rituxan®), trastuzumab (Herceptin®), ibritumomab tiuxetan (Zevalin®), tositumomab (Bexxar®), cetuximab (C-225, Erbitux®), bevacizumab (Avastin®), gemtuzumab ozogamicin (Mylotarg®), alemtuzumab (Campath®), and BL22. Monoclonal antibodies are used in the treatment of a wide range of cancers including breast cancer (including advanced metastatic breast cancer), colorectal cancer (including advanced and/or metastatic colorectal cancer), ovarian cancer, lung cancer, prostate cancer, cervical cancer, melanoma and brain tumours. Other examples include anti-CTLA4 antibodies (e.g. Ipilimumab), anti-PD1 antibodies, anti-PDL1 antibodies, anti-TIMP3 antibodies, anti-LAG3 antibodies, anti-B7H3 antibodies, anti-B7H4 antibodies or anti-B7H6 antibodies.

Active specific immunotherapy typically involves the use of cancer vaccines. Cancer vaccines have been developed that comprise whole cancer cells, parts of cancer cells or one or more antigens derived from cancer cells. Cancer vaccines, alone or in combination with one or more immuno- or chemotherapeutic agents are being investigated in the treatment of several types of cancer including melanoma, renal cancer, ovarian cancer, breast cancer, colorectal cancer, and lung cancer. Non-specific immunotherapeutics are useful in combination with cancer vaccines in order to enhance the body's immune response.

The immunotherapeutic treatment may consist of an adoptive immunotherapy as described by Nicholas P. Restifo, Mark E. Dudley and Steven A. Rosenberg "Adoptive immunotherapy for cancer: harnessing the T cell response, Nature Reviews Immunology, Volume 12, April 2012). In adoptive immunotherapy, the subject's circulating lymphocytes, or tumor infiltrated lymphocytes, are isolated in vitro, activated by lymphokines such as IL-2 or transuded with genes for tumor necrosis, and readministered (Rosenberg et al., 1988; 1989). The activated lymphocytes are most preferably be the subject's own cells that were earlier isolated from a blood or tumor sample and activated (or "expanded") in vitro. This form of immunotherapy has produced several cases of regression of melanoma and renal carcinoma.

In some embodiments, the methods of the present invention are suitable for determining whether a subject is eligible or not to a treatment with a radiotherapeutic agent. For example, when it is concluded that the subject has a cancer then the physician can take the choice to administer the subject with a radiotherapeutic agent.

The term "radiotherapeutic agent" as used herein, is intended to refer to any radiotherapeutic agent known to one of skill in the art to be effective to treat or ameliorate cancer, without limitation. For instance, the radiotherapeutic agent can be an agent such as those administered in brachytherapy or radionuclide therapy. Such methods can optionally further comprise the administration of one or more additional cancer therapies, such as, but not limited to, chemotherapies, and/or another radiotherapy.

The methods of the present invention are also suitable for determining the efficiency of an above mentioned treatment in the subject.

Thus, the invention also relates to a method for determining whether a subject achieve a response with a treatment comprising the steps of:
  i. apply a method according to the invention before the treatment;
  ii. apply a method according to the invention after the treatment;
  iii. comparing the values determined at step i) with the value determined at step and;
  iv. concluding that the subject suffers from a cancer when the level determined at step i) differ from the value determined at step ii).

The above mentioned methods of the present invention are particularly suitable for discriminating responder from non-responder. As used herein the term "responder" in the context of the present disclosure refers to a subject that will achieve a response, i.e. a subject where the cancer is eradicated, reduced or improved, or stabilized such that the disease is not progressing after the treatment. In responders where the cancer is stabilized, the period of stabilization is such that the quality of life and/or subjects' life expectancy is increased (for example stable disease for more than 6, 7, 8, 9, 10, 11, 12, 13, 14, 15, 16, 17, 18, 19, 20, 21, 22, 23, 24 or more months) in comparison to a subject that does not receive the treatment. A non-responder or refractory subject includes subjects for whom the cancer does not show reduction or improvement after treatment. Optionally the characterization of the subject as a responder or non-responder can be performed by reference to a standard or a training set. The standard may be the profile of a subject who is known to be a responder or non responder or alternatively may be a numerical value. Such predetermined standards may be provided in any suitable form, such as a printed list or diagram, computer software program, or other media. When it is concluded that the subject is a non responder, the physician could take the decision to stop the treatment to avoid any further adverse sides effects.

The methods of the present invention are also suitable for determining the efficiency of an above mentioned treatment in the subject.

Thus, the invention also relates to a method for determining whether a subject who suffered from a cancer has a relapse after a treatment comprising the steps of:
  i. apply a method according to the invention after the treatment;
  ii. comparing the values determined at step i) with a predetermined reference value and;
  iii. concluding that the subject has a relapse when the level determined at step i) differ from the predetermined reference value.

As used herein, the term "relapse" refers to the return of a cancer or the signs and symptoms of a cancer after a period of improvement in which no cancer could be detected. The likely relapse occurs is that a few of the original cancer cells survived the initial treatment. Alternatively, this is because cancer cells spread to other parts of the body and were too small to be detected during the follow-up taking place after the treatment (metastasis).

The invention will be further illustrated by the following figures and examples. However, these examples and figures should not be interpreted in any way as limiting the scope of the present invention.

FIGURES

FIG. 1: Difference between Healthy vs Cancer subjects as regards to the size profile. Size profile as determined by Whole Genome deep sequencing of cfDNA extracted from a cancer patient (full line) and a healthy individuals (dotted line) show differences all along 20 to 400 nt. For instance, three ranges that mostly discriminate healthy to cancer patient cfDNA size profile are here characterized. The first one (between 98 and 158 nt) in which fragment levels are higher for Cancer patients, a second (168-218) and a third one (320-400) where fragment level are lower as compared to Healthy subjects Either size at specific nucleotide number, size range %, ratio of size at specific nucleotide number over size range %, or size range ratio calculation enable to demonstrate discrimination. While the size profile is peaking at the same nucleotide numbers (160-167 nucleotides) there is a shift to the left of the size profile or to fragments shortening. Note, there is a specific sub-population of cfDNA fragments peaking at about 307 nt for cancer subjects and around 322 nt for healthy subjects. An illustration of applying this observation towards a screening test for cancer is presented in the following tables.

Figure 2:
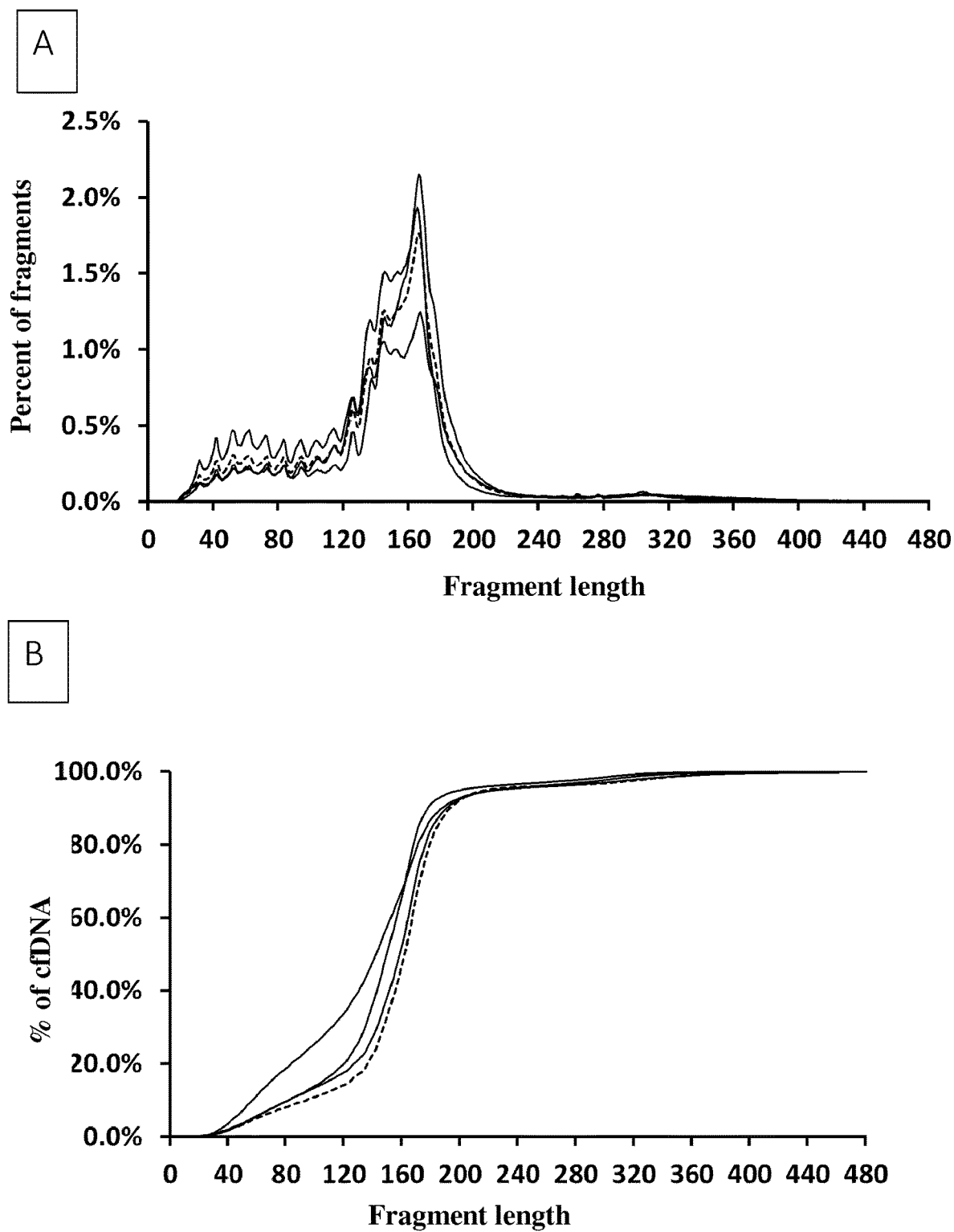

FIG. 2: Size profile of cfDNA from cancer patients (n=3) and mean of healthy individuals (n=4) as determined by SSP-S (A) and corresponding cumulative values (B). Full lines, cancer patients; dotted line, mean healthy individuals.

Figure 3:
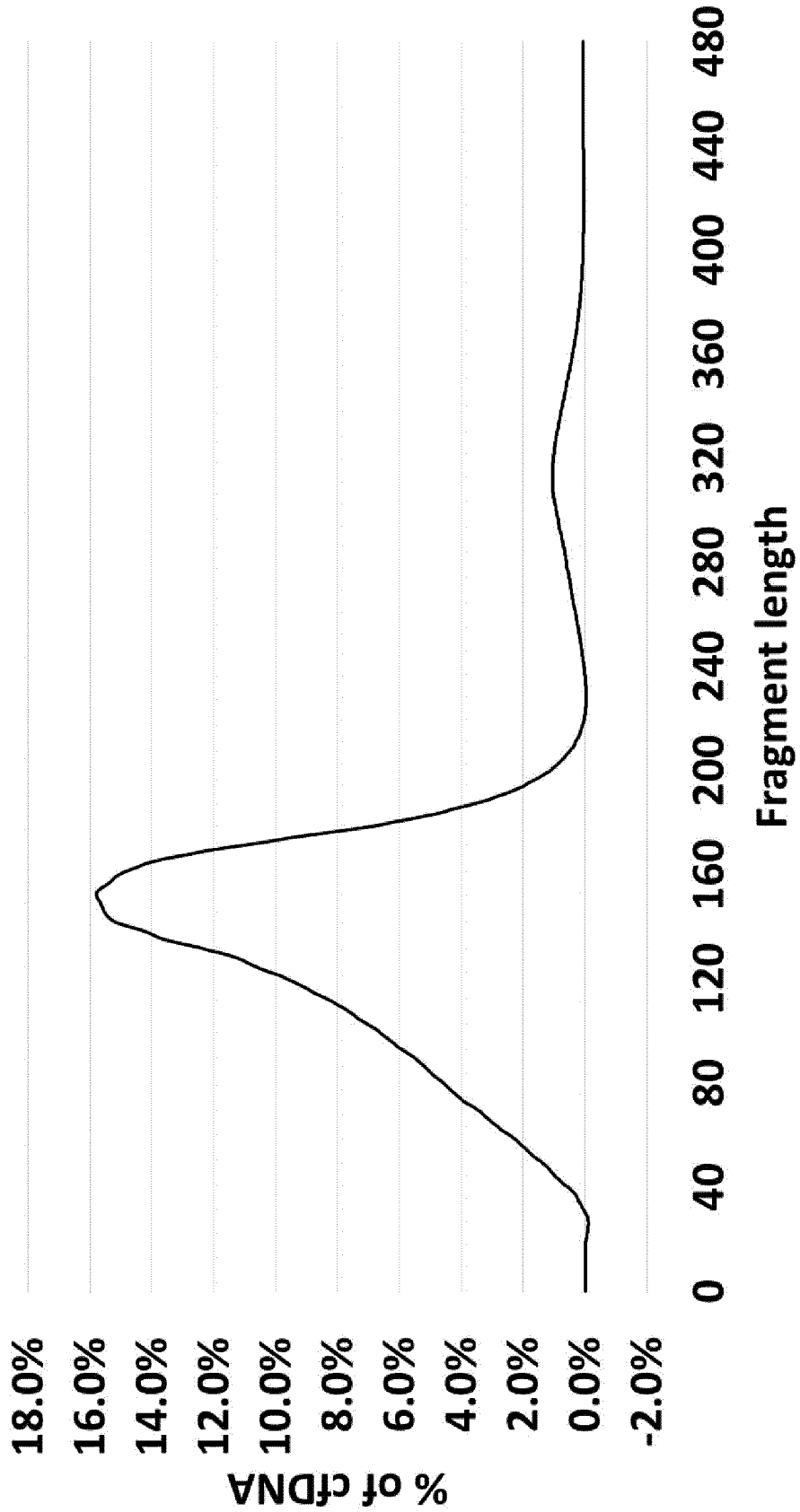

FIG. 3: CfDNA fragment size plotted in function to the difference between the cumulative values as determined in FIG. 2B between cancer patient mean and healthy subject mean (cancer minus healthy). This figure highlights the size range and value showing the highest screening capacity.

Figure 4:
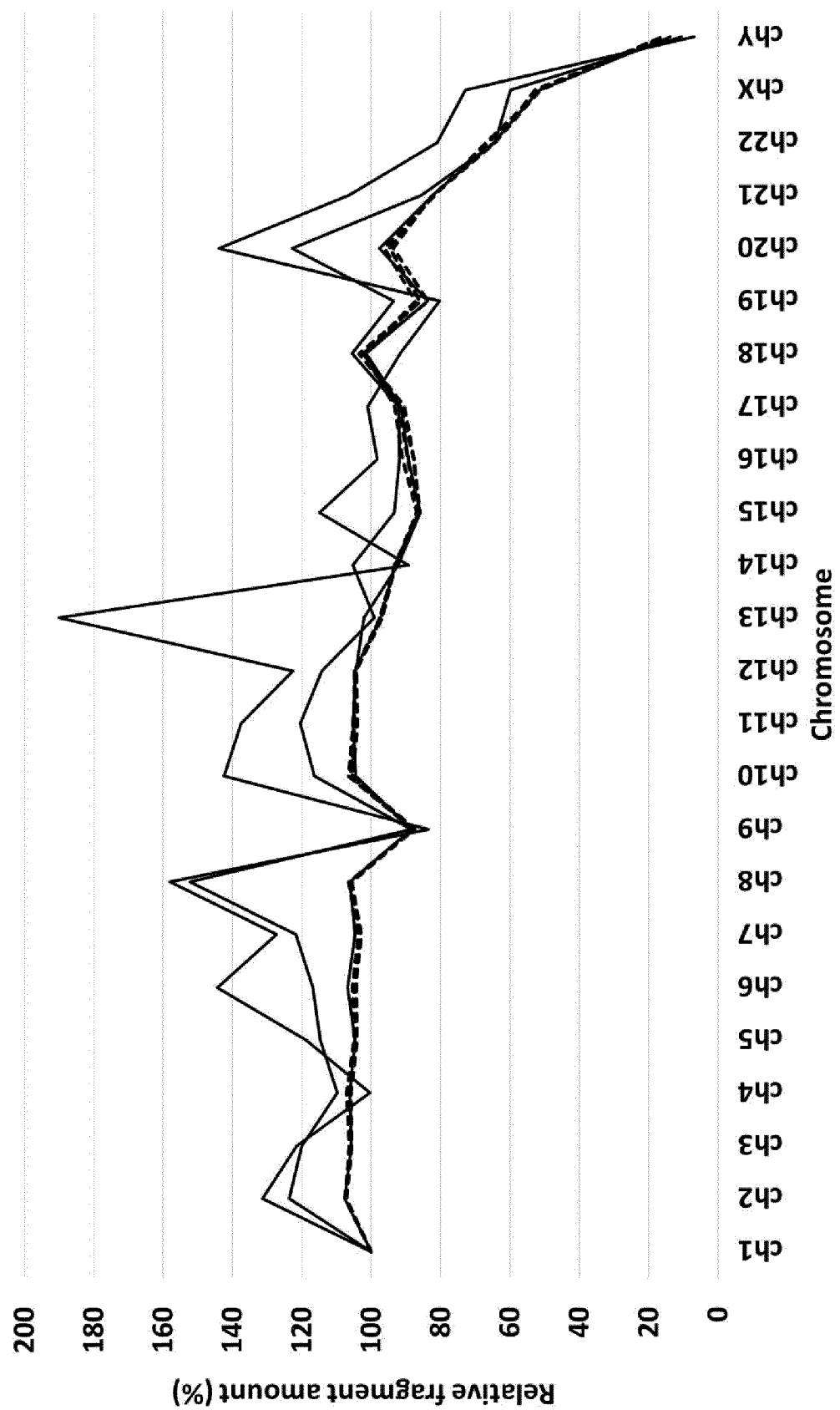

FIG. 4: Relative fragment amount deriving from each individual chromosome. Relative amount was determined from reads out obtained by SSP sequencing. They were normalized from both chromosome size and chromosome 1 value. Full lines, cancer patients; dotted line, healthy individuals.

TABLE 1

Illustrative example of the difference of the size profile between a cancer patient and a healthy individuals for different fragment of nucleotides.

| Length (nt) | Cancer reads sample 1 | Healthy reads sample 5 | cancer sample 1 reads | Healthy sample 5 reads | Cancer % fragments vs 166 nt | Healthy % fragments vs 166 nt |
|---|---|---|---|---|---|---|
| 166 | 99428 | 59533 | 1.90% | 2.04% | 100.0% | 100.0% |
| 53 | 12525 | 6164 | 0.24% | 0.21% | 12.6% | 10.4% |
| 104 | 14709 | 4935 | 0.28% | 0.17% | 14.8% | 8.3% |
| 114 | 19326 | 5803 | 0.37% | 0.20% | 19.4% | 9.7% |
| 126 | 35932 | 12294 | 0.69% | 0.42% | 36.1% | 20.7% |
| 137 | 61536 | 20537 | 1.18% | 0.70% | 61.9% | 34.5% |
| 145 | 79094 | 33148 | 1.51% | 1.13% | 79.5% | 55.7% |
| 156 | 79345 | 39505 | 1.52% | 1.35% | 79.8% | 66.4% |

TABLE 1-continued

Illustrative example of the difference of the size profile between a cancer patient and a healthy individuals for different fragment of nucleotides.

| Length (nt) | Cancer reads sample 1 | Healthy reads sample 5 | cancer sample 1 reads | Healthy sample 5 reads | Cancer % fragments vs 166 nt | Healthy % fragments vs 166 nt |
|---|---|---|---|---|---|---|
| 307 | 2171 | 997 | 0.04% | 0.03% | 2.2% | 1.7% |
| 322 | 1207 | 1290 | 0.02% | 0.04% | 1.2% | 2.2% |

Determination of the proportion of cfDNA fragments in respect to the 166 nt peak value obtained by SSP-S. The highest differences are observed for the value (reads) of the fragment of 114, 137, 145, 156 nt. As a consequence, discrimination index could be for a individuals to be tested: 114 nt, >15%; 137 nt, >50%; 145 nt, >70%; difference between 156 and 145 nt, <5%; and 307 nt > 322 nt.

TABLE 2

Sequencing analysis from SSP (specifics ranges).

| | | Amount in a range (%) Data from SSP sequencing analysis | | | | | | | | | | |
|---|---|---|---|---|---|---|---|---|---|---|---|---|
| | | <120 | >120 | 165-250 | 119-120 | <100 | >100 | <120 | >20 | 20-120 | >100 | 30-120 | 145-250 |
| Cancer patients | 1e KPLEXII 35 | 19.6% | 80.4% | 23.8% | 0.7% | 13.5% | 86.5% | 19.6% | 100% | 19.6% | 0.87 | 19.5% | 55.5% |
| | 2e KPLEXII 77 | 17.4% | 82.6% | 37.0% | 0.5% | 13.1% | 86.9% | 17.4% | 100% | 17.4% | 86.9% | 17.2% | 66.1% |
| | 3e KPLEXII 96 | 33.2% | 66.8% | 24.0% | 0.9% | 24.9% | 75.1% | 33.2% | 100% | 33.2% | 75.1% | 32.9% | 44.3% |
| | Mean | 23.4% | 76.6% | 28.3% | 0.7% | 17.2% | 82.8% | 23.4% | 100.0% | 23.4% | 82.8% | 23.2% | 55.3% |
| | SD | 0.09 | 0.09 | 0.08 | 0.00 | 0.07 | 0.07 | 0.09 | 0.00 | 0.09 | 0.07 | 0.08 | 0.11 |
| Healthy individuals | 5e EFS 5158 | 14.4% | 85.6% | 44.6% | 0.4% | 10.9% | 89.1% | 14.4% | 100% | 14.4% | 89.1% | 14.2% | 71.8% |
| | 6e EFS 1822 | 11.3% | 88.7% | 41.2% | 0.3% | 8.1% | 91.9% | 11.3% | 100% | 11.3% | 91.9% | 11.1% | 73.1% |
| | 7e EFS 1830 | 13.4% | 86.6% | 43.4% | 0.3% | 10.3% | 89.7% | 13.4% | 100% | 13.4% | 89.7% | 13.1% | 72.7% |
| | 8e EFS 1865 | 16.2% | 82.9% | 43.2% | 0.4% | 12.6% | 87.4% | 16.2% | 100% | 16.2% | 87.4% | 16.0% | 69.7% |
| | Mean | 13.8% | 86.0% | 43.1% | 0.3% | 10.5% | 89.5% | 13.8% | 100.0% | 13.8% | 89.5% | 13.6% | 71.8% |
| | SD | 0.02 | 0.02 | 0.01 | 0.00 | 0.02 | 0.02 | 0.02 | 0.00 | 0.02 | 0.02 | 0.0 | 0.02 |
| Fold from mean | | 1.7 | 1.1 | 1.5 | 2.0 | 1.6 | 1.1 | 1.7 | | 1.7 | 1.1 | 1.7 | 1.3 |
| discriminating power | | + | + | ++ | + | + | + | + | | ++ | ++ | ++ | ++ |
| proposed intra-range threshold | | 17% | 82.7% | 40% | 0.4% | 12.8% | 87% | 17% | | 17% | 87% | 17% | 65% |

Proportion of the cfDNA amount in a range or a fraction of cfDNA fragment size. Values under < and > x columns correspond to the % of fragments being lower or higher than x nucleotides from the total number of cfDNA fragments being lower than 1000 nt. Fold from mean corresponds to the value of the ratio of the mean calculated from the four healthy individuals to the mean calculated from the three cancer patients. The highest is the fold from mean, the highest is the discrimination power. The discriminating power is defined as absent (0), weak (+), moderate (++) and high (+++). The proposed proportion threshold corresponds to the proportion of the fragment size range enabling cancer screening. SD = standard deviation.

TABLE 3

Sequencing analysis from SSP (specific ratio of ranges).

| | | Ratio of range | | | | | | | |
|---|---|---|---|---|---|---|---|---|---|
| | | <120/>120 | 165-250/ 119-120 | 119-120/ 165-250 | <100/>100 | <120/>20 | 120-155/ 155-180 | 20-120/>100 | 30-120/ 145-250 |
| Cancer patients | 1e KPLEXII 35 | 0.24 | 34.02 | 0.029 | 0.16 | 0.20 | 1.13 | 0.23 | 0.35 |
| | 2e KPLEXII 77 | 0.21 | 73.92 | 0.014 | 0.15 | 0.17 | 0.68 | 0.20 | 0.26 |
| | 3e KPLEXII 96 | 0.50 | 28.10 | 0.036 | 0.33 | 0.33 | 1.18 | 0.44 | 0.74 |
| | Mean | 0.32 | 45.35 | 0.026 | 0.21 | 0.23 | 1.00 | 0.29 | 0.45 |
| | SD | 0.16 | 24.92 | 0.011 | 0.10 | 0.09 | 0.27 | 0.13 | 0.26 |
| Healthy individuals | 5e EFS 5158 | 0.17 | 125.50 | 0.008 | 0.12 | 0.14 | 0.58 | 0.16 | 0.20 |
| | 6e EFS 1822 | 0.13 | 127.44 | 0.008 | 0.09 | 0.11 | 0.65 | 0.12 | 0.15 |
| | 7e EFS 1830 | 0.15 | 137.71 | 0.007 | 0.11 | 0.13 | 0.60 | 0.15 | 0.18 |
| | 8e EFS 1865 | 0.20 | 117.65 | 0.009 | 0.14 | 0.16 | 0.59 | 0.19 | 0.23 |
| | Mean | 0.16 | 127.08 | 0.01 | 0.12 | 0.14 | 0.61 | 0.15 | 0.19 |
| | SD | 0.03 | 8.26 | 0.00 | 0.02 | 0.02 | 0.03 | 0.03 | 0.03 |
| Fold from mean | | 1.97 | 2.80 | 3.3153 | 1.81 | 1.69 | 1.64 | 1.87 | 2.37 |
| discriminating power | | + | +++ | +++ | + | + | + | + | ++ |
| proposed ratio threshold | | 0.11 | 110 | 0.010 | 0.15 | 0.17 | 0.66 | 0.2 | 0.24 |

Discrimination between cancer patient and healthy individuals by determining ratio of values of various size range. Ratio are expressed as % of the numerator over the denominator. Fold from mean corresponds to the ratio of the mean calculated from the four healthy individuals to the mean calculated from the three cancer patients. The highest is the fold from mean, the highest is the discrimination power. The discriminating power is defined as absent (0), weak (+), moderate (++) and high (+++). The proposed ratio threshold corresponds to ratio of values of two size range enabling cancer discrimination and screening. SD = standard deviation.

TABLE 4

Sequencing analysis from SSP (specific groups).

| | | ratio of size ranges | | | | |
|---|---|---|---|---|---|---|
| | | 145-250/>30 | 120-145/120-250 | 120-145/120-180 | 101-145/120-250 | 101-145/120-180 |
| Cancer patients | 1e KPLEXII 35 | 0.56 | 0.31 | 0.34 | 0.38 | 0.41 |
| | 2e KPLEXII 77 | 0.66 | 0.20 | 0.23 | 0.25 | 0.29 |
| | 3e KPLEXII 96 | 0.44 | 0.32 | 0.37 | 0.44 | 0.51 |
| | Mean | 0.55 | 0.27 | 0.31 | 0.36 | 0.41 |
| | SD | 0.11 | 0.07 | 0.07 | 0.10 | 0.11 |
| Healthy individuals | 5e EFS 5158 | 0.72 | 0.16 | 0.20 | 0.20 | 0.25 |
| | 6e EFS 1822 | 0.73 | 0.18 | 0.21 | 0.22 | 0.25 |
| | 7e EFS 1830 | 0.73 | 0.16 | 0.20 | 0.20 | 0.24 |
| | 8e EFS 1865 | 0.70 | 0.16 | 0.20 | 0.20 | 0.25 |
| | Mean | 0.72 | 0.17 | 0.20 | 0.20 | 0.25 |
| | SD | 0.02 | 0.01 | 0.01 | 0.01 | 0.01 |
| | Fold from mean | 1.30 | 1.64 | 1.53 | 1.75 | 1.63 |
| | discriminating power | ++ | ++ | ++ | +++ | +++ |
| | proposed threshold | 0.67 | 0.19 | 0.22 | 0.23 | 0.26 |

| | | ratio of size ranges | | | | |
|---|---|---|---|---|---|---|
| | | 101-145/145-250 | 100-250/101-145 | 100-250/120-145 | 46-60/20-250 | 46-60/145-250 |
| Cancer patients | 1e KPLEXII 35 | 0.54 | 2.80 | 3.46 | 0.03 | 0.05 |
| | 2e KPLEXII 77 | 0.30 | 4.26 | 5.35 | 0.03 | 0.04 |
| | 3e KPLEXII 96 | 0.63 | 2.57 | 3.58 | 0.06 | 0.13 |
| | Mean | 0.49 | 3.21 | 4.13 | 0.04 | 0.08 |
| | SD | 0.17 | 0.92 | 1.06 | 0.02 | 0.05 |
| Healthy individuals | 5e EFS 5158 | 0.23 | 5.24 | 6.51 | 0.03 | 0.04 |
| | 6e EFS 1822 | 0.26 | 4.79 | 5.68 | 0.02 | 0.02 |
| | 7e EFS 1830 | 0.23 | 5.21 | 6.29 | 0.02 | 0.03 |
| | 8e EFS 1865 | 0.24 | 5.11 | 6.44 | 0.03 | 0.05 |
| | Mean | 0.24 | 5.09 | 6.23 | 0.03 | 0.03 |
| | SD | 0.01 | 0.21 | 0.38 | 0.01 | 0.01 |
| | Fold from mean | 2.03 | 1.59 | 1.51 | 1.58 | 2.18 |
| | discriminating power | ++ | ++ | ++ | 0 | + |
| | proposed threshold | 0.28 | 4.5 | 5.5 | | 0.04 |

Amount in a range or proportion of fragment in a specific size range expressed as % of the total cfDNA fragment amount. Fold from mean corresponds to the ratio of the mean calculated from the four healthy individuals to the mean calculated from the three cancer patients. The highest is the fold from mean, the highest is the discrimination power. The discriminating power is defined as absent (0), weak (+), moderate (++) and high (+++). The proposed ratio threshold corresponds to the ratio of values of various size range enabling cancer discrimination and screening. SD = standard deviation.

TABLE 5

Sequencing analysis from SSP (specific ratio of groups).

| | | ratio of size ranges | | | | |
|---|---|---|---|---|---|---|
| | | 145-250/>30 | 120-145/120-250 | 120-145/120-180 | 101-145/120-250 | 101-145/120-180 |
| Cancer patients | 1e KPLEXII 35 | 0.56 | 0.31 | 0.34 | 0.38 | 0.41 |
| | 2e KPLEXII 77 | 0.66 | 0.20 | 0.23 | 0.25 | 0.29 |
| | 3e KPLEXII 96 | 0.44 | 0.32 | 0.37 | 0.44 | 0.51 |
| | Mean | 0.55 | 0.27 | 0.31 | 0.36 | 0.41 |
| | SD | 0.11 | 0.07 | 0.07 | 0.10 | 0.11 |
| Healthy individuals | 5e EFS 5158 | 0.72 | 0.16 | 0.20 | 0.20 | 0.25 |
| | 6e EFS 1822 | 0.73 | 0.18 | 0.21 | 0.22 | 0.25 |
| | 7e EFS 1830 | 0.73 | 0.16 | 0.20 | 0.20 | 0.24 |
| | 8e EFS 1865 | 0.70 | 0.16 | 0.20 | 0.20 | 0.25 |
| | Mean | 0.72 | 0.17 | 0.20 | 0.20 | 0.25 |
| | SD | 0.02 | 0.01 | 0.01 | 0.01 | 0.01 |
| | Fold from mean | 1.30 | 1.64 | 1.53 | 1.75 | 1.63 |
| | discriminating power | ++ | ++ | ++ | +++ | +++ |
| | proposed threshold | 0.67 | 0.19 | 0.22 | 0.23 | 0.26 |

| | | ratio of size ranges | | | | |
|---|---|---|---|---|---|---|
| | | 101-145/145-250 | 100-250/101-145 | 100-250/120-145 | 46-60/20-250 | 46-60/145-250 |
| Cancer patients | 1e KPLEXII 35 | 0.54 | 2.80 | 3.46 | 0.03 | 0.05 |
| | 2e KPLEXII 77 | 0.30 | 4.26 | 5.35 | 0.03 | 0.04 |
| | 3e KPLEXII 96 | 0.63 | 2.57 | 3.58 | 0.06 | 0.13 |

TABLE 5-continued

Sequencing analysis from SSP (specific ratio of groups).

|  |  |  |  |  |  |  |
|---|---|---|---|---|---|---|
|  | Mean | 0.49 | 3.21 | 4.13 | 0.04 | 0.08 |
|  | SD | 0.17 | 0.92 | 1.06 | 0.02 | 0.05 |
| Healthy individuals | 5e EFS 5158 | 0.23 | 5.24 | 6.51 | 0.03 | 0.04 |
|  | 6e EFS 1822 | 0.26 | 4.79 | 5.68 | 0.02 | 0.02 |
|  | 7e EFS 1830 | 0.23 | 5.21 | 6.29 | 0.02 | 0.03 |
|  | 8e EFS 1865 | 0.24 | 5.11 | 6.44 | 0.03 | 0.05 |
|  | Mean | 0.24 | 5.09 | 6.23 | 0.03 | 0.03 |
|  | SD | 0.01 | 0.21 | 0.38 | 0.01 | 0.01 |
| Fold from mean |  | 2.03 | 1.59 | 1.51 | 1.58 | 2.18 |
| discriminating power |  | ++ | ++ | ++ | 0 | + |
| proposed threshold |  | 0.28 | 4.5 | 5.5 |  | 0.04 |

Discrimination between cancer patient and healthy individuals by determining ratio of values of various size range. Fold from mean corresponds to the ratio of the mean calculated from the four healthy individuals to the mean calculated from the three cancer patients. The highest is the fold from mean, the highest is the discrimination power. The discriminating power is defined as absent (0), weak (+), moderate (++) and high (+++). The proposed ratio threshold corresponds to the ratio of values of two size ranges enabling cancer discrimination and screening. SD = standard deviation.

TABLE 6

Sequencing analysis from SSP (specific ratio of fragments).

Ratio of values at pecific size sequencing read ratio

|  |  | 168/56 | 168/120 | 168/100 | 118/130 | 166/156 | 167/143 | 120/100 | 28/250 | 170/160 | 120/145 |
|---|---|---|---|---|---|---|---|---|---|---|---|
| Cancer patients | 1e KPLEXII 35 | 8.9 | 4.5 | 7.5 | 0.5 | 1.2 | 1.3 | 1.7 | 3.2 | 0.80 | 0.24 |
|  | 2e KPLEXII 77 | 10.8 | 8.8 | 11.1 | 0.6 | 1.5 | 1.9 | 1.3 | 4.2 | 1.08 | 0.19 |
|  | 3e KPLEXII 96 | 3.3 | 2.6 | 3.5 | 0.7 | 1.3 | 1.2 | 1.4 | 4.5 | 1.01 | 0.45 |
|  | Mean | 7.6 | 5.3 | 7.4 | 0.6 | 1.3 | 1.5 | 1.4 | 4.0 | 1.0 | 0.3 |
|  | SD | 3.9 | 3.2 | 3.8 | 0.1 | 0.1 | 0.4 | 0.2 | 0.7 | 0.1 | 0.1 |
| Healthy individuals | 5e EFS 5158 | 12.6 | 11.5 | 14.8 | 0.7 | 1.5 | 2.1 | 1.3 | 5.6 | 1.21 | 0.16 |
|  | 6e EFS 1822 | 18.8 | 13.0 | 17.4 | 0.6 | 1.4 | 1.9 | 1.3 | 4.0 | 1.10 | 0.12 |
|  | 7e EFS 1830 | 15.3 | 13.7 | 19.8 | 0.7 | 1.5 | 2.1 | 1.4 | 9.4 | 1.17 | 0.13 |
|  | 8e EFS 1865 | 9.3 | 10.5 | 13.4 | 0.7 | 1.5 | 2.1 | 1.3 | 6.0 | 1.24 | 0.17 |
|  | Mean | 14.0 | 12.2 | 16.4 | 0.7 | 1.5 | 2.1 | 1.3 | 6.3 | 1.2 | 0.1 |
|  | SD | 4.0 | 1.5 | 2.9 | 0.1 | 0.0 | 0.1 | 0.1 | 2.3 | 0.1 | 0.0 |
| Fold from mean |  | 1.8 | 2.3 | 2.2 | 1.1 | 1.1 | 1.4 | 1.1 | 1.6 | 1.2 | 2.0 |
| discriminating power |  | + | ++ | ++ | 0 | 0 | 0 | 0 | 0 | 0 | + |
| proposed threshold |  | 9 | 9 | 13 |  |  |  |  |  |  | 0.18 |

Ratio of values at pecific size sequencing read ratio

|  |  | 120/28 | 120/101 | 165/250 | 250/165 | 165/119 | 145/20 | 168/20 | 145/56 | 56/250 | 120/250 |
|---|---|---|---|---|---|---|---|---|---|---|---|
| Cancer patients | 1e KPLEXII 35 | 5.32 | 1.56 | 88.9 | 0.011 | 5.89 | 21.76 | 23.89 | 8.08 | 8.68 | 17.15 |
|  | 2e KPLEXII 77 | 2.47 | 1.20 | 95.8 | 0.010 | 9.97 | 13.06 | 21.63 | 6.51 | 8.44 | 10.38 |
|  | 3e KPLEXII 96 | 3.41 | 1.30 | 38.7 | 0.026 | 2.80 | 7.59 | 8.72 | 2.84 | 12.09 | 15.46 |
|  | Mean | 3.7 | 1.4 | 74.5 | 0.016 | 6.2 | 14.1 | 18.1 | 5.8 | 9.7 | 14.3 |
|  | SD | 1.5 | 0.2 | 31.2 | 0.01 | 3.6 | 7.1 | 8.2 | 2.7 | 2.0 | 3.5 |
| Healthy individuals | 5e EFS 5158 | 2.37 | 1.19 | 144.7 | 0.007 | 11.72 | 14.94 | 27.29 | 6.91 | 12.14 | 13.28 |
|  | 6e EFS 1822 | 3.35 | 1.27 | 177.9 | 0.006 | 15.11 | 27.39 | 43.66 | 11.78 | 9.41 | 13.54 |
|  | 7e EFS 1830 | 1.35 | 1.23 | 164.3 | 0.006 | 14.16 | 10.41 | 18.43 | 8.64 | 11.33 | 12.66 |
|  | 8e EFS 1865 | 2.11 | 1.12 | 126.4 | 0.008 | 11.52 | 12.29 | 22.10 | 5.16 | 14.19 | 12.59 |
|  | Mean | 2.3 | 1.2 | 153.3 | 0.007 | 13.1 | 16.3 | 27.9 | 8.1 | 11.8 | 13.0 |
|  | SD | 0.8 | 0.1 | 22.5 | 0.001 | 1.8 | 7.7 | 11.1 | 2.8 | 2.0 | 0.5 |
| Fold from mean |  | 1.6 | 1.1 | 2.1 | 2.4 | 2.1 | 1.2 | 1.5 | 1.4 | 1.2 | 1.1 |
| discriminating power |  | 0 | 0 | ++ | ++ | + | 0 | 0 | 0 | 0 | 0 |
| proposed threshold |  |  |  | 120 | 0.009 | 11 |  |  |  |  |  |

Discrimination between cancer patients and healthy individuals by determining ratio of values at various specific size. Fold from mean corresponds to the ratio of the mean calculated from the four healthy individuals to the mean calculated from the three cancer patients. The highest is the fold from mean, the highest is the discrimination power. The discriminating power is defined as absent (0), weak (+), moderate (++) and high (+++). Size range ratio with 0 discriminating power illustrate that only specific selected ratio enable high discriminating power. The proposed ratio threshold corresponds to ratio of the value of two specific sizes enabling cancer discrimination and screening. SD = standard deviation.

TABLE 7

Sequencing analysis from SSP (specific ratio on peak).

| | | | Ratio of value at one specific length to the peaking value sequencing read ratio | | | | | |
| | | | 120/peak | | 115/peak | | 130/peak | |
| | | Length at peak | 120/peak | peak/120 | 115/peak | peak/115 | 130/peak | peak/130 |
|---|---|---|---|---|---|---|---|---|
| Cancer patients | 1e KPLEXII 35 | 165 | 0.19 | 5.19 | 0.19 | 5.22 | 0.33 | 2.99 |
| | 2e KPLEXII 77 | 166 | 0.11 | 9.47 | 0.11 | 8.94 | 0.15 | 6.55 |
| | 3e KPLEXII 96 | 167 | 0.38 | 2.64 | 0.37 | 2.69 | 0.48 | 2.09 |
| | Mean | | 0.23 | 5.76 | 0.23 | 5.62 | 0.32 | 3.88 |
| | SD | | 0.14 | 3.45 | 0.13 | 3.14 | 0.16 | 2.36 |
| Healthy individuals | 5e EFS 5158 | 167 | 0.19 | 5.19 | 0.09 | 11.01 | 0.12 | 8.67 |
| | 6e EFS 1822 | 167 | 0.07 | 13.41 | 0.08 | 12.55 | 0.12 | 8.35 |
| | 7e EFS 1830 | 168 | 0.07 | 13.68 | 0.08 | 12.41 | 0.10 | 9.85 |
| | 8e EFS 1865 | 167 | 0.10 | 10.50 | 0.10 | 9.80 | 0.11 | 8.86 |
| | Mean | | 0.11 | 10.70 | 0.09 | 11.44 | 0.11 | 8.93 |
| | SD | | 0.1 | 3.9 | 0.01 | 1.3 | 0.0 | 0.6 |
| Fold from mean | | | 2.1 | 1.9 | 2.5 | 2.0 | 2.9 | 2.3 |
| discriminating power | | | + | 0 | + | + | +++ | +++ |
| proposed threshold | | | 0.1 | | 0.1 | 9.5 | 0.13 | 8 |

Discrimination between cancer patients and healthy individuals by determining ratio of the values of a two specific fragment sizes. Peak correspond here to a size of 166 nt. Fold from mean corresponds to the ratio of the mean calculated from the four healthy individuals to the mean calculated from the three cancer patients. The highest is the fold from mean, the highest is the discrimination power. The discriminating power is defined as absent (0), weak (+), moderate (++) and high (+++). The proposed threshold corresponds to the ratio of the two fragment size enabling cancer screening. SD = standard deviation

TABLE 8

Sequencing analysis from SSP (range and ratio of range on peak).

| | | range to peak ratio (120-155)/value at the peak | Ratio range with peak value 120-155/100 to peak |
|---|---|---|---|
| Cancer patients | 1e KPLEXII 35 | 20.03 | 63.0% |
| | 2e KPLEXII 77 | 12.77 | 54.4% |
| | 3e KPLEXII 96 | 23.73 | 58.5% |
| | Mean | 18.84 | 58.6% |
| | SD | 5.58 | 0.04 |
| Healthy individuals | 5e EFS 5158 | 11.91 | 51.5% |
| | 6e EFS 1822 | 13.00 | 53.5% |
| | 7e EFS 1830 | 12.01 | 49.9% |
| | 8e EFS 1865 | 12.10 | 51.5% |
| | Mean | 12.25 | 51.6% |
| | SD | 0.5 | 0.015 |
| Fold from mean | | 1.5 | 1.1 |
| discriminating power | | + | + |
| proposed threshold | | 13.1 | 65% |

Discrimination between cancer patients and healthy individuals by determining ratio of a size range over the value of a precise size or the ratio of two size ranges. Peak correspond here to the size of 166 nt. Fold from mean corresponds to the ratio of the mean calculated from the four healthy individuals to the mean calculated from the three cancer patients. The highest is the fold from mean, the highest is the discrimination power. The discriminating power is defined as absent (0), weak (+), moderate (++) and high (+++). The proposed threshold corresponds to the ratio of the two fragment size or ranges enabling cancer screening. SD = standard deviation.

TABLE 9

Q-PCR analysis.

| | | | Data of q-PCR | | | | | |
| | | | Range | | | | Ratio of range | |
| | Origin | Patients number | 101-145 | 185-249 | 101-185 | <145 | 101-185/185-249 | 101-145/185-249 |
|---|---|---|---|---|---|---|---|---|
| Healthy individuals | CfDNA Extract | 9 | 9.00% | 25.58% | 18.1% | 63.7% | 0.71 | 0.35 |
| | | 10 | 6.60% | — | 11.8% | 66.0% | — | — |
| | | 11 | 0.00% | — | — | 52.9% | — | — |
| | | 12 | 10.25% | — | — | — | — | — |
| | | MEAN | 6.46% | 25.58% | 14.98% | 60.86% | 0.71 | 0.35 |
| | | SD | 4.57% | — | 4.45% | 7.00% | — | — |
| Cancer patients | | 13 | 18.4% | 20.7% | 26.7% | 68.5% | 1.29 | 0.89 |
| | | 14 | | 15.5% | 14.0% | 72.1% | 0.90 | |
| | | 15 | 18.1% | 10.3% | 25.6% | 78.8% | 2.49 | 1.77 |
| | | 16 | 14.6% | | 30.2% | 66.0% | — | — |
| | | 17 | 9.8% | — | | 71.2% | — | — |
| | | 18 | 19.2% | — | — | 73.8% | — | — |
| | | 19 | 15.7% | — | — | | — | — |
| | | MEAN | 15.95% | 15.47% | 24.10% | 71.73% | 1.56 | 1.33 |
| | | SD | 3.50% | 5.23% | 7.03% | 4.42% | | |
| Fold from mean | | | 2.47 | 1.65 | 1.61 | 1.18 | 2.20 | 3.78 |
| discriminating power | | | + | + | + | + | ++ | ++ |
| proposed threshold | | | | 21% | | 66% | 0.8 | 0.7 |

TABLE 9-continued

Q-PCR analysis.

| | | Data of q-PCR | | | | | |
|---|---|---|---|---|---|---|---|
| | | Range | | | | Ratio of range | |
| Origin | Patients number | 101-145 | 185-249 | 101-185 | <145 | 101-185/185-249 | 101-145/185-249 |

Discrimination between cancer patients and healthy individuals by comparing proportion of the amount of fragments of specific size ranges and by determining ratio of the proportion of the amount of fragments of two specific size ranges by Q-PCR. Values of a fragment size range between two sizes are expressed as % from the total amount of fragment as determined by detecting an amplicon of 60 bp. Fold from mean corresponds to the ratio of the mean calculated from the four healthy individuals to the mean calculated from the three cancer patients. The highest is the fold from mean, the highest is the discrimination power. The discriminating power is defined as absent (0), weak (+), moderate (++) and high (+++). The proposed threshold corresponds to the value of a ratio enabling cancer screening. SD = standard deviation.

TABLE 10

Illustration of the enhancing performance for screening cancer by combining the discriminating power of three ratio and correlation of specific size ratio with the percent mutant cell free DNA in the three cancer patients.

| | | combination | | | | | |
|---|---|---|---|---|---|---|---|
| | patient number | 119-120/ 165-250 | 101-145/ 120-250 | 130/peak | fold difference from healthy mean | mA % | fold difference from the lowest mA % |
| healthy mean | 5, 6, 7, 8 | 0.01 | 0.2 | 0.11 | 0.0002 | 1 | 0% | |
| 2e KPLEXII 77 | 2 | 0.014 | 0.25 | 0.15 | 0.0005 | 2.6 | 7.2% | 1.0 |
| 1e KPLEXII 35 | 1 | 0.029 | 0.38 | 0.33 | 0.0038 | 18.9 | 25.70% | 7.1 |
| 3e KPLEXII 96 | 3 | 0.036 | 0.44 | 0.48 | 0.0075 | 37.5 | 79.4% | 14.2 |

Peak corresponds to the size at the maximal peak = 165 nt

TABLE 11

Selected calculations enabling discrimination between cancer patient and healthy subjects from circulating DNA size profile analysis by SSP sequencing.
SSP sequencing

| | threshold | screening capacity |
|---|---|---|
| Values at nucleotide size (%) | | |
| 120 | >0.19 | ** |
| 114 | >0.21 | ** |
| 322 | <0.044 | ** |
| 130 | >0.27 | ** |
| size range values (%) | | |
| 40 to 145 | >26 | ** |
| 170 to 370 | <30% | * |
| 119 to 120 | >35% | *** |
| 145 to 250 | <67% | ** |
| 165 to 250 | <40% | ** |
| 145 to 250 | <67% | ** |
| 165 to 250 | <40% | ** |
| values ratio | | |
| 119 to 120/194 to 370 | >0.04 | *** |
| 30 to 120/145 to 250 | >23% | ** |
| 119 to 120/165 to 250 | >0.01 | *** |
| peak at 100%/100 | >13 | ** |
| peak at 100%/130 | <8 | *** |
| 30 to 120/145 to 250 | >0.23 | ** |
| 119 to 120/165 to 250 | >0.008 | *** |
| 100 to 145/145 to 250 | >0.26 | ** |

Cancer screening capacity was distinguished from moderate (<100% difference, *), high (<200% difference, ) and very high (>200% increase, *).

TABLE 12

Selected differences among the relative amount of cfDNA fragments deriving from a single chromosome (Ch) which revealed discrimination between cancer and healthy subjects. The difference Ch4-Ch6 is always negative in case of cancer patients in contrast to the positive values obtained in healthy subjects, showing the highest screening capacity.

| | | Difference of relative fragment amount (%) | | | | |
|---|---|---|---|---|---|---|
| | | ch2-ch3 | ch2-ch5 | ch2-ch4 | ch4-ch7 | ch4-ch6 |
| Cancer | 1e_SS | 3.7 | 9.0 | 13.9 | −12.0 | −7.1 |
| | 2e_SS | 2.1 | 3.1 | 1.6 | 1.4 | −0.7 |
| | 3e_SS | 9.8 | 12.6 | 30.9 | −26.9 | −43.9 |
| | Mean | 5.2 | 8.2 | 15.5 | −12.5 | −17.2 |
| Healthy | 5e_SS | 1.0 | 2.2 | 0.3 | 3.3 | 1.7 |
| | 6e_SS | 1.4 | 3.0 | 0.5 | 3.1 | 2.3 |
| | 7e_SS | 1.2 | 2.8 | 0.5 | 4.0 | 2.1 |
| | 8e_SS | 1.8 | 3.2 | 1.5 | 3.0 | 1.5 |
| | mean | 1.4 | 2.8 | 0.7 | 3.3 | 1.9 |

Values are expressed in percentage as presented in FIG. 4.

EXAMPLE

Example 1

Material & Methods
Samples

Cancer patients are colorectal cancer patients. Healthy individuals are volunteer blood donor from EFS.

Plasma Isolation and cfDNA Extraction

All samples were collected in EDTA tubes of 4 mL. The blood was centrifuged at 1200 g at 4° C. for 10 min. The supernatants were isolated in sterile 1.5 ml Eppendorf tubes and centrifuged at 16000 g at 4° C. for 10 min. Afterwards, the plasma was either immediately handled for DNA extraction or stored at −20° C. cfDNA was extracted from 1 ml of plasma using the QiaAMP Circulating Nucleic Acids Kit (Qiagen) as per the manufacturer's protocol for Conversant Bio samples and QIAmp DNA Mini Blood kit (Qiagen) according to the "Blood and body fluid protocol" and our detailed protocol31 for ICM samples. DNA extracts were kept at −20° C. until use. DNA yield was quantified with a Qubit Fluorometer (Invitrogen).

Preparation of Sequencing Libraries

Between 0.5 ng and 10.0 ng of cfDNA were used as input for all libraries. Library amplification for all samples was monitored by real-time PCR to avoid over-amplification, and was typically terminated after 4-6 cycles.

Preparation of Single Strand Sequencing Library

Single stranded sequencing libraries were prepared with a protocol adapted from Gansauge et al 24. Briefly, A double strand adapter, Adapter2, was prepared by combining 4.5 µL TE (pH 8), 0.5 µL 1M NaCl, 10 µL 500 uM oligo Adapter2.1, and 10 µL 500 uM oligo Adapter2.2, incubating at 95° C. for 10 seconds, and ramping to 14° C. at a rate of 0.1° C./second. Purified cfDNA fragments were dephosphorylated by combining 2× CircLigase II buffer (Epicentre), 5 mM MnCl¬2, and 1U FastAP (Thermo Fisher) with 0.5-10 ng cfDNA fragments in 20 µL reaction volume and incubating at 37° C. for 30 minutes. Fragments were then denatured by heating to 95° C. for 3 minutes, and were immediately transferred to an ice bath. The reaction was supplemented with 5 pmol biotin-conjugated adapter oligo CL78, 20% PEG-6000 (w/v), and 200U CircLigase II (Epicentre) for a total volume of 40 µL, and was incubated overnight with rotation at 60° C., heated to 95° C. for 3 minutes, and placed in an ice bath. For each sample, 20 µL MyOne Cl beads (Life Technologies) were twice washed in bead binding buffer (BBB) (10 mM Tris-HCl [pH 8], 1M NaCl, 1 mM EDTA [pH 8], 0.05% Tween-20, and 0.5% SDS), and resuspended in 250 µL BBB. Adapter-ligated fragments were bound to the beads by rotating for 60 minutes at room temperature. Beads were collected on a magnetic rack and the supernatant was discarded. Beads were washed once with 500 µL wash buffer A (WBA) (10 mM Tris-HCl [pH 8], 1 mM EDTA [pH 8], 0.05% Tween-20, 100 mM NaCl, 0.5% SDS) and once with 500 µL wash buffer B (WBB) (10 mM Tris-HCl [pH 8], 1 mM EDTA [pH 8], 0.05% Tween-20, 100 mM NaCl). Beads were combined with 1× Isothermal Amplification Buffer (NEB), 2.5 uM oligo CL9, 250 uM (each) dNTPs, and 24U Bst 2.0 DNA Polymerase (NEB) in a reaction volume of 50 µL, incubated with gentle shaking by ramping temperature from 15° C. to 37° C. at 1° C./minute, and held at 37° C. for 10 minutes. After collection on a magnetic rack, beads were washed once with 200 µL WBA, resuspended in 200 µL of stringency wash buffer (SWB) (0.1×SSC, 0.1% SDS), and incubated at 45° C. for 3 minutes. Beads were again collected and washed once with 200 µL WBB. Beads were then combined with 1× CutSmart Buffer (NEB), 0.025% Tween-20, 100 uM (each) dNTPs, and 5U T4 DNA Polymerase (NEB) and incubated with gentle shaking for 30 minutes at room temperature. Beads were washed once with each of WBA, SWB, and WBB as described above. Beads were then mixed with 1× CutSmart Buffer (NEB), 5% PEG-6000, 0.025% Tween-20, 2 uM double strand Adapter2, 1 mM ATP, and 10U T4 DNA Ligase (NEB), and incubated with gentle shaking for 2 hours at room temperature. Beads were washed once with each of WBA, SWB, and WBB as described above, and resuspended in 25 µL TET buffer (10 mM Tris-HCl [pH 8], 1 mM EDTA [pH 8], 0.05% Tween-20). Second strands were eluted from beads by heating to 95° C., collecting beads on a magnetic rack, and transferring the supernatant to a new tube. Library amplification was monitored by real-time PCR, requiring an average of 4-6 cycles per library.

Size Profile Analysis by Deep Sequencing

All libraries were sequenced on HISeq 2000 or NextSeq 500 instruments (Illumina). Barcoded single-end reads (SR) and the individual Barcoded paired-end reads (PE) were aligned to the human reference genome (GRCH37, 1000 Genomes phase 2 technical reference, ftp://ftp.1000genomes .ebi.ac.uk/vol1/ftp/technical/reference/ phase2_reference_assembly_sequence/) using the ALN algorithm in BWA v0.7.10. PE reads were further processed with BWA SAMPE to resolve ambiguous placement of read pairs or to rescue missing alignments by a more sensitive alignment step around the location of one placed read end. Aligned SR and PE data were stored in BAM format using the samtools API. BAM files for each sample were merged across lanes and sequencing runs. Since SSP-S provides size profile based upon detection of ssDNA fragment, length unit is consequently number of nucleotide (nt).

Size Profile Analysis by Q-PCR

The oligonucleotides primers target DNA sequences of increasing size in human KRAS region intron 2 described in supplementary data, table S5. The size of the amplicons were 60 bp, 73 bp, 101 bp, 145 bp, 185 bp, 249 bp and 400 bp. The reverse primer used was the same for all sizes. Our q-PCR experiments followed the MIQE guideline45. q-PCR amplifications were performed at least in duplicate in a 25 µL reaction volume on a CFX96 instrument using the CFX manager software 3.0 (Bio-Rad). Each PCR reaction mixture was composed of 12.5 µL PCR mix (Bio-Rad Super mix SYBR Green), 2.5 µL of each amplification primer (0.3 pmol/µL, final concentration), 2.5 µL PCR-analyzed water, and 5 µL DNA extract. Thermal cycling consisted of three repeated steps: a 3-min Hot-start Polymerase activation denaturation step at 95° C., followed by 40 repeated cycles at 95° C. for 10 s, and then at 60° C. for 30 s. Melting curves were obtained by increasing the temperature from 55° C. to 90° C. with a plate reading every 0.2° C. As calibrators for quantification, serial dilutions of genomic DNA from the DIFI cell line were used. Sample concentrations were extrapolated from this standard curve. Negative controls were used in duplicate for each experiment. The efficiency of these primers was assessed using as reference a human genomic DNA purchased from Promega. This DNA was quantified by q-PCR using the different primer systems showed a gaussian distribution with a maximum amplification with primers targeting the sequence of 145 nt. Each concentration obtained for each size was normalized based on the concentration observed using the primers targeting the 145 nt sequence. The DNA concentration corresponds to the number of amplicons obtained for each targeted size. Size range fractions were calculated by subtracting the amount obtained with the larger amplicon from the amount obtained with the shorter amplicon divided by the highest amplicon amount (60 bp minus 73 bp divided by 60 bp, 60 bp minus 101 bp divided by 60 bp). Since q-PCR provides size profile based upon detection of ssDNA fragments, length unit is consequently number of nucleotide (nt). The fraction corresponding to cfDNA fragments higher than 400 nt or 249 nt corresponds to the amount obtained when targeting sequence of 400 nt or 249 nt.

Results

In the tables 1 to 11, the inventors illustrated the power of the method. Indeed, they analysed different combination of fragments (isolated fragments, range of fragments, ratio) and always demonstrated that they are difference in the level of these fragments between cancer and healthy subjects.

Indeed, the inventors observe differences between cancer subjects and healthy subjects in the size profile obtained with methods denaturating cell free DNA such as Q-PCR or sequencing from single strand library preparation (SSP) (FIG. 1).

They observed that resulting denaturated cell free nucleic acid amount at precise sizes or size ranges are specific to both groups. In particular, denaturated cell free DNA from cancer patient exhibit higher proportion of fragments of size between 100 and 160 nucleotides (or peak as defined above) or between 260 and 320 nucleotides as compared to healthy individuals and lower proportion of fragments of size between 160 and 250, between 145 and 160, and between 300 and 400 nucleotides as compared to healthy individuals (FIG. 1 and Tables 1 to 11).

Comparisons between cancer subjects and healthy subjects can be made from the respective level at precise length of single stranded DNA fragment or length of group of single stranded DNA fragments (see Tables 1 to 10). Ratio at specific nucleotide length of single stranded DNA fragment or length of group of single stranded DNA fragments can also be made.

All or a few discriminating specific values or ratio can be combined to obtain higher screening performance, by an algorithm/modelling.

Results also show that there is clear correlation of specific values or ranges from cancer patient denaturated cell free DNA with the frequency of mutant cell free DNA among total cell free DNA (percent mutant ratio, mA %) (Table 10). This buttress the notion that those values or ranges are specific to cancer patients.

Example 2

Selection of new calculation providing discrimination between cancer and healthy individuals are shown in Table 11. Values observed at specific nucleotide size (%), or obtained in calculating of specific size range (%), or obtained in calculating various values ratio are classified upon low (*), moderate () and high (*) screening capacity. A threshold is proposed for each selected sizing based screening marker.

Selection was eased by determining from the size profile (FIG. 2A) cumulative values in function of fragment lengths (FIG. 2B) and the difference between cancer patient and the healthy subject mean (calculated from #5, #6, #7 and #8 homogeneous values) cumulative values (FIG. 3). Two discriminating zones are revealed: a major difference between 40 and 200 nt peaking at 155 nt (up to 16%), and a minor difference between 220 and 390 nt peaking at 310 nt (up to 1%). For the peak at 155, 16% means that cancerous patients have 16% more fragments of the size of 155 nt than healthy patients.

Example 3

CfDNA derive from all genomic DNA and then from all chromosomes. SSP-S can reveal the specific cfDNA amount deriving from each chromosome. FIG. 4 showed the relative number of cfDNA fragments deriving from each chromosome (Ch) as determined by SSP-sequencing of cancer and healthy individuals. Since cfDNA amount should rely on DNA molecule length, the relative amount was normalized from both specific chromosome length and chromosome 1 value. This data suggested us to claim two methods enabling higher screening capacity:

1. Since the amount of the cfDNA fragment from cancer subjects in some Ch are higher than that from healthy subjects it would be preferable in order to increase the screening capacity, to calculate the selected fragment number values at specific cfDNA fragment sizes, ranges or ratio as above described, within the readout from such Ch (i.e. #8, 10 or 20).
2. FIG. 4 enables to compare cfDNA number found in different Ch. The Table 12 shows the selected differences among the relative amount of cfDNA fragments deriving from a single chromosome (Ch) which revealed discrimination between cancer and healthy subjects. Note, the difference Ch4-Ch6 is always negative in case of cancer patients in contrast to the positive values obtained in healthy subjects. Ch4-Ch6 showed the highest screening capacity.

Since only a poor difference is observed when analyzing #2 cancer patient sample which showed the lowest concentration in mutant fragment, we may speculate that these methods are more relevant for testing plasma sample with a significant concentration of malignant cell derived cfDNA.

REFERENCES

Throughout this application, various references describe the state of the art to which this invention pertains. The disclosures of these references are hereby incorporated by reference into the present disclosure.
1. Thierry, A. R., El Messaoudi, S., Gahan, P. B., Anker, P. & Stroun, M. Origins, structures, and functions of circulating DNA in oncology. Cancer Metastasis Rev. 35, 347-376 (2016).
2. Stroun, M. et al. Neoplastic characteristics of the DNA found in the plasma of cancer patients. Oncology 46, 318-322 (1989).
3. Wan, J. C. M. et al. Liquid biopsies come of age: towards implementation of circulating tumour DNA. Nat. Rev. Cancer 17, 223-238 (2017).
4. Diehl, F. et al. Detection and quantification of mutations in the plasma of patients with colorectal tumors. Proc. Natl. Acad. Sci. U.S.A. 102, 16368 (2005).
5. Mandel, P. & Metais, P. [Not Available]. C. R. Seances Soc. Biol. Fil. 142, 241-243 (1948).
6. Stroun, M. & Anker, P. Nucleic acids spontaneously released by living frog auricles. Biochem. J. 128, 100P (1972).
7. Leon, S. A., Shapiro, B., Sklaroff, D. M. & Yaros, M. J. Free DNA in the Serum of Cancer Patients and the Effect of Therapy. Cancer Res. 37, 646-650 (1977).
8. Mouliere, F., El Messaoudi, S., Pang, D., Dritschilo, A. & Thierry, A. R. Multi-marker analysis of circulating cell-free DNA toward personalized medicine for colorectal cancer. Mol. Oncol. 8, 927-941 (2014).
9. Heitzer, E. et al. Establishment of tumor-specific copy number alterations from plasma DNA of patients with cancer. Int. J. Cancer J. Int. Cancer 133, 346 (2013).
10. Lo, Y. M. D. et al. Maternal Plasma DNA Sequencing Reveals the Genome-Wide Genetic and Mutational Profile of the Fetus. Sci. Transl. Med. 2, 61ra91-61ra91 (2010).
11. Holdenrieder, S. et al. Circulating Nucleosomes in Serum. Ann. N. Y. Acad. Sci. 945, 93-102 (2001).
12. Aucamp, J., Bronkhorst, A. J., Badenhorst, C. P. S. & Pretorius, P. J. A historical and evolutionary perspective on the biological significance of circulating DNA and extracellular vesicles. Cell. Mol. Life Sci. 73, 4355-4381 (2016).
13. Jiang, P. et al. Lengthening and shortening of plasma DNA in hepatocellular carcinoma patients. Proc. Natl. Acad. Sci. U.S.A. 112, E1317 (2015).
14. Underhill, H. R. et al. Fragment Length of Circulating Tumor DNA. PLoS Genet. 12, (2016).
15. Jahr, S. et al. DNA fragments in the blood plasma of cancer patients: quantitations and evidence for their origin from apoptotic and necrotic cells. Cancer Res. 61, 1659-1665 (2001).
16. Ivanov, M., Baranova, A., Butler, T., Spellman, P. & Mileyko, V. Non-random fragmentation patterns in circulating cell-free DNA reflect epigenetic regulation. BMC Genomics 16, S1 (2015).
17. Szerlong, H. J. & Hansen, J. C. Nucleosome distribution and linker DNA: connecting nuclear function to dynamic chromatin structure. Biochem. Cell Biol. Biochim. Biol. Cell. 89, 24 (2011).
18. Chandrananda, D., Thorne, N. P. & Bahlo, M. High-resolution characterization of sequence signatures due to non-random cleavage of cell-free DNA. BMC Med. Genomics 8, (2015).
19. Wang, B. G. et al. Increased Plasma DNA Integrity in Cancer Patients. Cancer Res. 63, 3966-3968 (2003).
20. Mouliere, F. et al. High Fragmentation Characterizes Tumour-Derived Circulating DNA. PLoS ONE 6, (2011).
21. Andersen, R. F., Spindler, K.-L. G., Brandslund, I., Jakobsen, A. & Pallisgaard, N. Improved sensitivity of circulating tumor DNA measurement using short PCR amplicons. Clin. Chim. Acta 439, 97-101 (2015).
22. Garlan, F. et al. Circulating Tumor DNA Measurement by Picoliter Droplet-Based Digital PCR and Vemurafenib Plasma Concentrations in Patients with Advanced BRAF-Mutated Melanoma. Target. Oncol. 12, 365-371 (2017).
23. Snyder, M. W., Kircher, M., Hill, A. J., Daza, R. M. & Shendure, J. Cell-free DNA comprises an in vivo nucleosome footprint that informs its tissues-of-origin. *Cell* 164, 57 (2016).
24. Burnham, P. et al. Single-stranded DNA library preparation uncovers the origin and diversity of ultrashort cell-free DNA in plasma. *Sci. Rep.* 6, 27859 (2016).
25. Sanchez C, Snyder M W, Tanos R et al. New insights into structural features and optimal detection of circulating tumor DNA determined by single-strand DNA analysis. npj Genomic Medicine 2018; 3(1):31.

The invention claimed is:
1. A method for treating cancer in a subject in need thereof, comprising the steps of:
   i) extracting cell free DNA from a sample obtained from a subject;
   ii) denaturating the cell free DNA to obtain single stranded DNA fragments;
   iii) determining the levels of single stranded DNA fragments having a length ranging from 98 to 158 nucleotides and from 168-218 nucleotides; and
   iv) administering one or more cancer treatments to a subject identified as having
   a higher level than a predetermined reference value of at least one single stranded DNA fragment ranging from 98 to 158 nucleotides, and
   a lower level than a predetermined reference value of at least one single stranded DNA fragment having a length ranging from 168 to 218 nucleotides;
   wherein the one or more cancer treatments are selected from the group consisting of radiotherapy, chemotherapy, and immunotherapy.
2. The method of claim 1, wherein the cancer is colorectal cancer.
3. The method of claim 2, wherein the colorectal cancer is metastatic colorectal cancer.

* * * * *